(12) United States Patent
Tang et al.

(10) Patent No.: US 12,338,263 B2
(45) Date of Patent: Jun. 24, 2025

(54) ANTIBACTERIAL AMINOGLYCOSIDE DERIVATIVES

(71) Applicant: ZHUOHE PHARMACEUTICAL GROUP CO., LTD, Jiangsu (CN)

(72) Inventors: Dongdong Tang, Shanghai (CN); Zhigang Huang, Shanghai (CN); Cheng Li, Shanghai (CN); Charles Z. Ding, Shanghai (CN); Shuhui Chen, Shanghai (CN)

(73) Assignee: ZHUOHE PHARMACEUTICAL GROUP CO., LTD, Jiangsu (CN)

( * ) Notice: Subject to any disclaimer, the term of this patent is extended or adjusted under 35 U.S.C. 154(b) by 877 days.

(21) Appl. No.: 17/615,307

(22) PCT Filed: May 29, 2020

(86) PCT No.: PCT/CN2020/093436
§ 371 (c)(1),
(2) Date: Nov. 30, 2021

(87) PCT Pub. No.: WO2020/239096
PCT Pub. Date: Dec. 3, 2020

(65) Prior Publication Data
US 2022/0227802 A1    Jul. 21, 2022

(30) Foreign Application Priority Data

May 30, 2019  (CN) .......................... 201910463155.1
Apr. 16, 2020  (CN) .......................... 202010299506.2

(51) Int. Cl.
*C07H 15/224* (2006.01)
*A61P 31/04* (2006.01)

(52) U.S. Cl.
CPC ............ *C07H 15/224* (2013.01); *A61P 31/04* (2018.01)

(58) Field of Classification Search
CPC ....... C07H 15/224; C07H 15/22; A61P 31/04; A61K 31/7028
USPC .......................................................... 514/36
See application file for complete search history.

(56) References Cited

U.S. PATENT DOCUMENTS 9,688,711 B2    6/2017   Aggen et al.

FOREIGN PATENT DOCUMENTS

| CN | 107987111 A | 4/2018 | |
|---|---|---|---|
| WO | 2010132777 A2 | 11/2010 | |
| WO | 2010147836 A1 | 12/2010 | |
| WO | WO2017/206947 A1 * | 12/2017 | ............. A61P 31/04 |

OTHER PUBLICATIONS

Eljaaly et al, Drugs, Feb. 2019, 79, 243-269.*
AU2020285280—Australian Examination Report No. 1; Aug. 26, 2022.
CA3142199—Examiner's Report; Canadian Patent Office; Dec. 12, 2022.
EA202193266—First Office Action; Eurasian Patent Office; Dec. 12, 2022 (original document and English translation).
EA202193266—Second Office Action; Eurasian Patent Office; Jun. 8, 2023 (original document and English translation).
EP20815146.4—European search report; Aug. 2, 2022.
IN202117057486—First Examination Report; Indian Patent Office; Jun. 20, 2022.
JP2021-571459—Notice of Reasons for Refusal; Japanese Patent Office; Dec. 15, 2022 (original document and English translation).
KR10-2021-7040773—Request for the Submission of an Opinion; Korean Patent Office; Oct. 31, 2023 (original document and English translation).
MX2021014544—1st Substantive Official Action; Mexican Patent Office; Jul. 16, 2024 (original document and English translation).
Ukrainian Application No. a 202107603—First Office Action; Ukranian Patent Office; Sep. 19, 2022 (original document and English translation).
Eljaaly, K. et al., Plazomicin: A Novel Aminoglycoside for the Treatment of Resistant Gram Negative Bacterial Infections, Drugs, vol. 79, pp. 243-269 Feb. 6, 2019.
English Translation of WO 20171206947.
English Translation of Abstract CN107987111A.

* cited by examiner

*Primary Examiner* — Ganapathy Krishnan
(74) *Attorney, Agent, or Firm* — Forge IP, PLLC

(57) ABSTRACT

Disclosed are a new class of antibacterial aminoglycoside derivatives, pharmaceutical compositions containing such compounds, and application thereof in the preparation of drugs for treating diseases related to bacterial infections. Specifically disclosed are a compound represented by formula (II), pharmaceutically acceptable salts thereof, and isomers thereof.

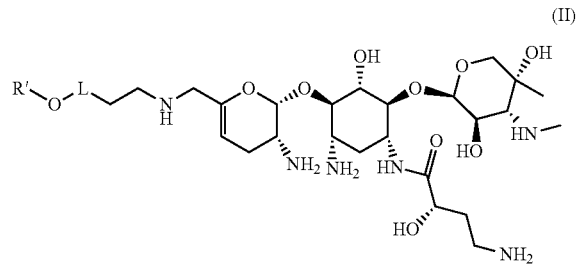

2 Claims, 4 Drawing Sheets

ANTIBACTERIAL AMINOGLYCOSIDE DERIVATIVES

This application claims the following priority of:
Application number CN201910463155.1 filed on May 30, 2019; and
Application number CN202010299506.2 filed on Apr. 16, 2020.

TECHNICAL FIELD

The present invention relates to the field of medicine, in particular to a new class of aminoglycoside derivatives, pharmaceutically acceptable salts or isomers thereof, pharmaceutically acceptable compositions thereof, and their use in manufacturing a medicament for the treatment of bacterial infection-related diseases.

BACKGROUND ARTS

A particular interest in modern drug discovery is the development of novel small-molecular orally-bioavailable drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and RNAs are potential drug targeting sites, the number of targets revealed from genome sequencing efforts is effectively doubled. These observations unlock a new world of opportunities for the pharmaceutical industry to target RNA with small molecules.

Modern biochemistry and molecular biology studies have revealed that the binding of 30S subunit of bacterial ribosome to tRNA is one of the key steps in protein synthesis. So far, the crystal structures of the ribosomal 30S subunit of at least two bacteria (*Thermus thermophiles* and *Escherichia coli*) have been successfully reported. From the crystal structures, three sites that bind to tRNA can be clearly identified: aminoacyl site A, peptite site P, and E (Exit) site. Aminoglycoside medicines specifically bind toA site of the 16S rRNA decoding region of the 30S subunit of bacterial ribosome to cause mistranslation of mRNA, thereby interfering with protein synthesis to kill pathogenic bacteria. Aminoglycoside medicines are highly effective broad-spectrum antibiotics and are the most commonly used anti-infective medicines. Most aminoglycoside medicines have expected pharmacokinetic properties and have synergistic effects with other anti-infective medicines, making them excellent varieties for the treatment of life-threatening infections. In the past few decades, many varieties of this type of antibiotics have been clinically popular.

The history of aminoglycoside medicines originated from the discovery of streptomycin in 1944. Later, a series of landmark compounds (kanamycin, gentamicin, tobramycin) were successfully launched, and the status of aminoglycoside medicines in the treatment of gram-negative bacterial infections were established. Between the 1970s and 1990s, the semi-synthetic aminoglycoside antibiotics of dibekacin, amikacin, netilmicin, isepamicin and etimicin appeared one after another, indicating that aminoglycoside antibiotics that are effective against the bacteria resistant to early antibiotic and have low adverse reactions can be successfully obtained through semi-synthetic pathways, but the development of aminoglycoside antibiotics has been slowing down. Meanwhile, people have conducted extensive basic and clinical research on aminoglycoside medicines, especially their bactericidal mechanism and drug resistance mechanism, which not only gives people a deeper understanding of this type of antibiotics, but also provides a theoretical basis for our clinical rational use of medicines, reducing drug-resistant bacteria, and designing new aminoglycoside medicines against drug-resistant bacteria with these research results.

Aminoglycoside medicines are glycosides formed by connecting amino sugars and amino cyclic alcohols through oxygen bridges. There are streptomycin from *Streptomyces*, natural aminoglycoside medicines such as gentamicin from *Micromonospora*, and semi-synthetic aminoglycoside medicines such as etimicin and amikacin, all of which are broad-spectrum antibacterial drugs. Aminoglycoside medicines are mainly used for systemic infections caused by sensitive aerobic gram-negative bacteria. Although a variety of cephalosporins and quinolones have been widely used in clinical practice in recent years, aminoglycoside medicines are still used for treatment of serious infections caused by aerobic gram-negative bacteria because they have a longer PAE for common gram-negative bacteria such as *Pseudomonas aeruginosa, Klebsiella pneumoniae*, and *Escherichia coli*.

With the long-term and large-scale use of aminoglycoside medicines in the clinic, serious drug resistance problems inevitably arise in this class of medicines. At the same time, the common side effects of aminoglycoside medicines such as ototoxicity and nephrotoxicity also limit use of aminoglycoside medicines. In recent years, some medicine molecules that can solve the problem of traditional antibiotic resistance have emerged, such as the newly developed plazomicin (WO2009067692) by Achaogen, which has completed the third phase of clinical research.

The present invention aims to solve the problems of severe drug resistance due to inactivating enzymes and the existence of ototoxicity and nephrotoxicity for traditional antibiotics such as etimicin, amikacin, gentamicin and the like. A class of novel aminoglycoside medicines with broader antibacterial spectrum and better activity is prepared by a simpler synthetic method compared with the prior art.

SUMMARY OF INVENTION

The present invention provides a compound represented by formula (II), a pharmaceutically acceptable salt thereof, or an isomer thereof:

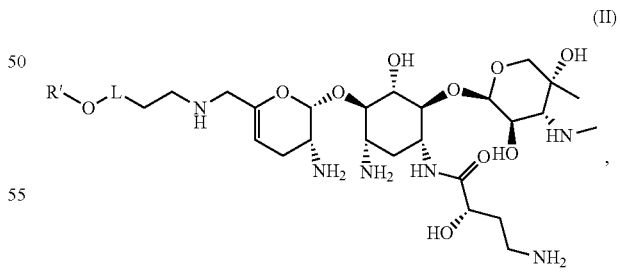

wherein,
R' is

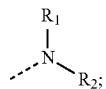

L is —O—CH₂—CH₂— or —CH₂—;

R₁ is H or C₁₋₃alkyl;

R₂ is H, C₁₋₃alkyl or

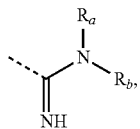

wherein C₁₋₃alkyl is optionally substituted by 1, 2 or 3 substituent(s) independently selected from the group consisting of F, Cl, Br, I, —OH, —OCH₃—CN, —NH₂ and —NO₂;

R$_a$ and R$_b$ each independently is H, —C(=O)—NH₂, —C(=O)—C₁₋₃alkyl or C₁₋₃alkyl, wherein —C(=O)—C₁₋₃alkyl and C₁₋₃alkyl are optionally substituted by 1, 2 or 3 R; and each R is independently F, Cl, Br, I, —OH, —OCH₃, —CN or —NH₂.

The present invention provides a compound represented by formula (I), a pharmaceutically acceptable salt thereof, or an isomer thereof:

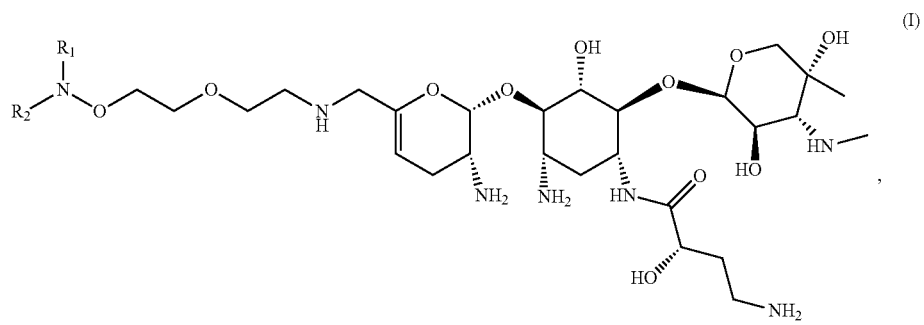

(I)

wherein, R₁ is H or C₁₋₃alkyl;

R₂ is H, C₁₋₃ alkyl or

wherein C₁₋₃ alkyl is optionally substituted by 1, 2 or 3 substituent(s) independently selected from the group consisting of F, Cl, Br, I, —OH, —OCH₃, —CN, —NH₂ and —NO₂;

R$_a$ and R$_b$ each independently is H, —C(=O)—NH₂, —C(=O)—C₁₋₃ alkyl or C₁₋₃ alkyl, wherein —C(=O)—C₁₋₃ alkyl and C₁₋₃ alkyl are optionally substituted by 1, 2 or 3 R; and each R is independently F, Cl, Br, I, —OH, —OCH₃, —CN or —NH₂.

In some embodiments, the above compound has the structure represented by formula (I-1):

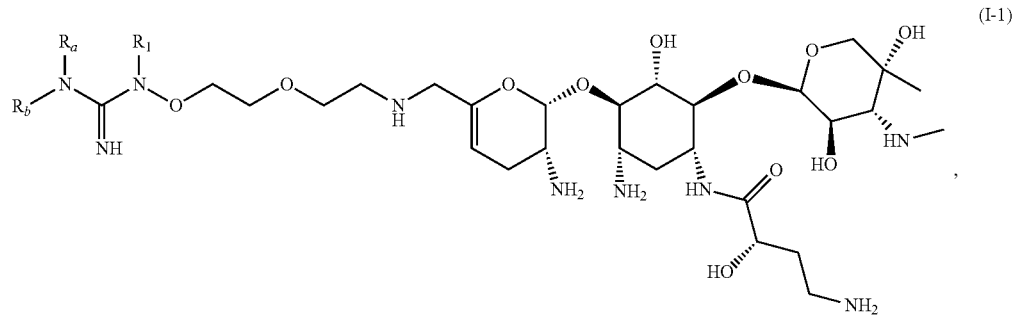

(I-1)

wherein $R_a$, $R_b$ and $R_1$ are as defined in the present invention.

In some embodiments, the above $R_1$ is H or $CH_3$, and the other variables are as defined in the present invention.

In some embodiments, the above $R_1$ is H, and the other variables are as defined in the present invention.

In some embodiments, the above compound has the structure represented by formula (I-2):

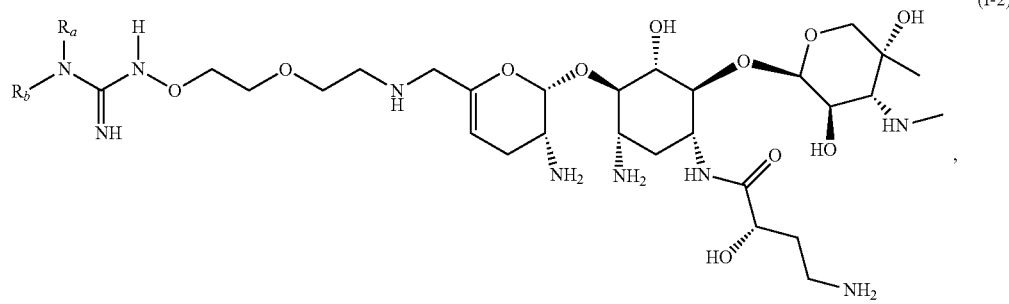

(I-2)

wherein $R_a$ and $R_b$ are as defined in the present invention.

In some embodiments, each of the above R is independently F or Cl, and the other variables are as defined in the present invention.

In some embodiments, each of the above R is independently F, and the other variables are as defined in the present invention.

In some embodiments, the above $R_a$ and $R_b$ each independently is H, —C(=O)—$NH_2$, —C(=O)—$CH_3$, —$CH_3$ or —$CH_2CH_3$, wherein —C(=O)—$CH_3$, —$CH_3$ and —$CH_2CH_3$ are optionally substituted by 1, 2 or 3 R; and R and the other variables are as defined in the present invention.

In some embodiments, the above $R_a$ and $R_b$ each independently is H, —C(=O)—$NH_2$, —C(=O)—$CH_3$, —$CH_3$, —$CH(R)_2$, —$CH_2CH_3$ or —$CH_2CH(R)_2$, and R and the other variables are as defined in the present invention.

In some embodiments, the above $R_a$ and $R_b$ each independently is H or

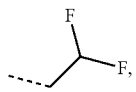

and the other variables are as defined in the present invention.

In some embodiments, the above $R_2$ is H, —$CH_3$, —$CH_2CH_3$ or

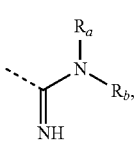

wherein —$CH_3$ and —$CH_2CH_3$ are optionally substituted by 1, 2 or 3 substituent(s) independently selected from the group consisting of F, Cl, Br, I, —OH, —$OCH_3$, —CN, —$NH_2$ and —$NO_2$, $R_a$ and $R_b$ and the other variables are as defined in the present invention.

In some embodiments, the above $R_2$ is

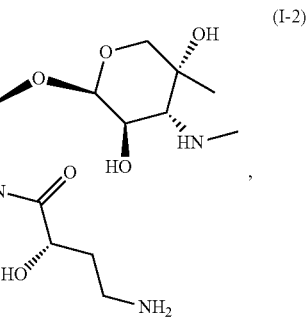

and the other variables are as defined in the present invention.

In some embodiments, the above structure unit

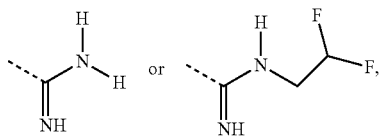

and the other variables are as defined in the present invention.

In some embodiments, the above structure unit

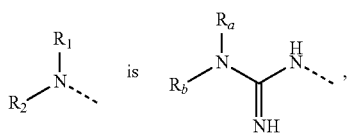

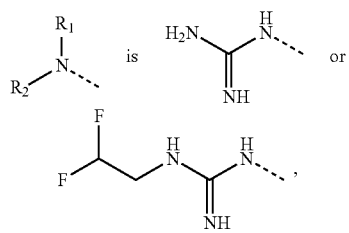

and the other variables are as defined in the present invention.

There are also some embodiments that come from any combination of the above variables.

In some embodiments, the above compound is:

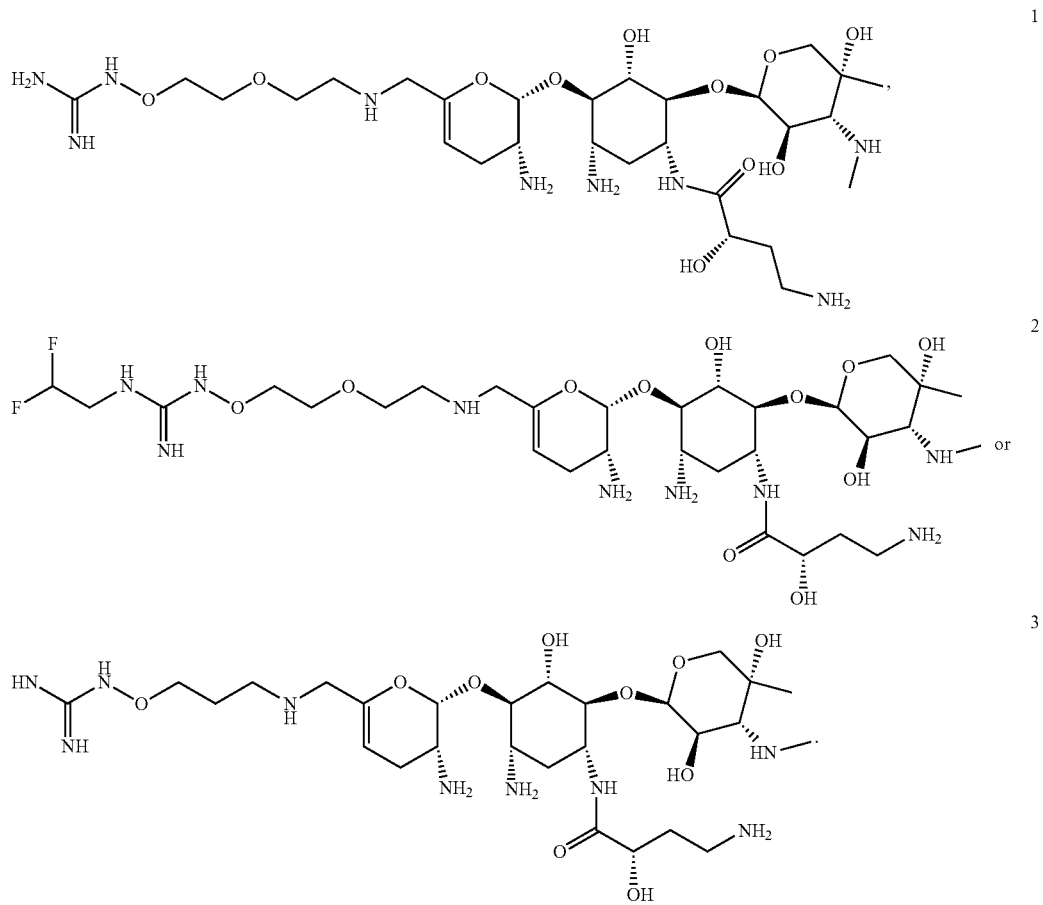

The present invention also provides a pharmaceutical composition, which includes a therapeutically effective amount of the above compound, its pharmaceutically acceptable salt or its isomer as an active ingredient, and a pharmaceutically acceptable carrier.

The present invention also provides use of the above compound, its pharmaceutically acceptable salt or its isomer, and the above pharmaceutical composition in the manufacture of a medicament for the treatment of bacterial infection-related diseases; and In some embodiments, the above bacteria are Carbapenem-resistant Enterobacteriaceae.

TECHNICAL EFFECTS

The present invention synthesizes the compound of formula (II) and its isomers through a simpler preparation method, and obtains a new class of aminoglycoside antibiotics to fight against the drug-resistant bacterial infection caused by super bacteria such as CRE (carbapenem-resistant Enterobacteriaceae), solving the problems of drug resistance due to inactivation enzyme and the existence of ototoxicity and nephrotoxicity for traditional antibiotics. Meanwhile, the compound of the present invention has a wider antibacterial spectrum, better activity, and no cytotoxicity.

DEFINITIONS AND DESCRIPTIONS

Unless otherwise specified, the following terms and phrases used herein are intended to have the following meanings. A specific term or phrase should not be considered indefinite or unclear without a special definition, but should be understood in its ordinary meaning. When a trade name appears herein, it is meant to refer to its corresponding commodity or its active ingredient.

The term "pharmaceutically acceptable" used herein refers to, for compounds, materials, compositions and/or dosage forms, within the scope of reliable medical judgment, suitable for use in contact with human and animal tissues without excessive toxicity, irritation, allergic reactions or other problems or complications, and commensurate with a reasonable benefit/risk ratio.

The term "pharmaceutically acceptable salt" refers to a salt of the compound of the present invention, which is prepared from a compound discovered in the present invention with specific substituent(s) and a relatively non-toxic acid or base. When the compound of the present invention contains a relatively acidic functional group, the base addition salt can be obtained by contacting the neutral form of the compound with a sufficient amount of base in a pure solution or a suitable inert solvent. Pharmaceutically acceptable base addition salts include sodium, potassium, calcium, ammonium, organic amine or magnesium salt or similar salts. When the compound of the present invention contains a relatively basic functional group, the acid addition salt can be obtained by contacting the neutral form of the compound with a sufficient amount of acid in a pure solution or suitable inert solvent. Examples of pharmaceutically acceptable acid addition salts include inorganic acid salts and organic acid salts. The inorganic acid includes, for example, hydrochloric acid, hydrobromic acid, nitric acid, carbonic acid, hydrogen carbonate, phosphoric acid, monohydrogen phosphate, dihydrogen phosphate, sulfuric acid, hydrogen sulfate, hydroiodic acid, phosphorous acid, etc. The organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid and the like. Examples of pharmaceutically acceptable acid addition salts also include salts of amino acids (such as arginine, etc.) and salts of organic acids such as glucuronic acid. Certain specific compounds of the present invention contain basic and acidic functional groups, so that they can be converted into any base or acid addition salt.

The pharmaceutically acceptable salt of the present invention can be synthesized from the parent compound containing acid or base radical by conventional chemical methods. Generally, such salts are prepared by reacting these compounds in free acid or base form with stoichiometric amounts of appropriate base or acid in water or organic solvent or a mixture of both.

There may exist specific geometric isomers or stereoisomers of the compounds of the present invention. The present invention contemplates all such compounds, including tautomers, cis-isomers and trans-isomers, (−)-enantiomers and (+)-enantiomers, (R)-enantiomers and (S)-enantiomers, diastereomers, (D)-isomers, (L)-isomers, their racemic mixtures and other mixtures, such as enantiomers or diastereomeric enriched mixtures. All these mixtures fall within the scope of the present invention. Additional asymmetric carbon atoms may be present in substituents such as alkyl. All these isomers and their mixtures are included in the scope of the present invention.

Unless otherwise specified, the term "enantiomer" or "optical isomer" refers to stereoisomers that are mirror images of each other.

Unless otherwise specified, the term "cis-, trans-isomer" or "geometric isomer" is caused by the inability to rotate freely due to double bonds or single bonds of ring-forming carbon atoms.

Unless otherwise specified, the term "diastereomer" refers to a stereoisomer in which the molecule has two or more chiral centers and the molecules are not mirror images to each other.

Unless otherwise specified, "(D)" or "(+)" means dextrorotation, "(L)" or "(−)" means levorotatory, and "(DL)" or "(±)" means racemic.

Unless otherwise specified, the wedge-shaped solid line bond ( ▰ ) and the wedge-shaped dashed line bond ( ▰ ) are used to represent the absolute configuration of a stereocenter, the straight solid line bond ( ▰ ) and the straight dashed line bond ( ▰ ) are used to represent the relative configuration of a stereocenter, and the wavy line ( ▰ ) is used to represent a wedge-shaped solid line bond ( ▰ ) or a wedge-shaped dashed line bond ( ▰ ), or the wavy line ( ▰ ) is used to represent a straight solid line bond ( ▰ ) and a straight dashed line bond ( ▰ ).

The compound of the present invention may be specific. Unless otherwise specified, the term "tautomer" or "tautomeric form" means that at room temperature, the isomers of different functional groups are in dynamic equilibrium and can be transformed into each other quickly. If tautomers are possible (such as in solution), the chemical equilibrium of tautomers can be reached. For example, proton tautomer (also called prototropic tautomer) includes interconversion through proton migration, such as keto-enol tautomerization and imine-enamine tautomerization. Valence tautomer includes mutual transformation by recombination of some bonding electrons. A specific example of keto-enol tautomerization is the tautomerization between two tautomers of pentane-2, 4-dione and 4-hydroxypent-3-en-2-one.

Unless otherwise specified, the terms "enriched in one isomer", "rich in isomers", "rich in one enantiomer" or "rich in enantiomers" refer to the content of one of the isomers or the enantiomers is less than 100%, and is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "isomer excess" or "enantiomeric excess" refers to the difference between the relative percentages of two isomers or two enantiomers. For example, if the content of one isomer or enantiomer is 90% and the content of the other isomer or enantiomer is 10%, the isomer or enantiomer excess (ee value) is 80%.

The optically active (R)- and (S)-isomers and D and L isomers can be prepared by chiral synthesis or chiral reagents or other conventional techniques. If an enantiomer of a compound of the present invention is desired, it can be prepared by asymmetric synthesis or derivatization with chiral auxiliaries, in which the resulting diastereomeric mixture is separated, and the auxiliary groups are removed to provide pure enantiomer desired. Alternatively, when the molecule contains a basic functional group (such as an amino group) or an acidic functional group (such as a carboxyl group), it forms a diastereomeric salt with a suitable optically active acid or base, then the diastereoisomers are resolved by a conventional method known in the art, and the pure enantiomers are recovered. In addition, the separation of enantiomers and diastereomers is usually accomplished through the use of chromatography, which employs a chiral stationary phase and is optionally combined with chemical derivatization (for example, the formation of carbaminate from amines). The compounds of the present invention may contain unnatural proportions of atomic isotopes on one or more of the atoms constituting the compound. For example, compounds can be labeled with radioisotopes, such as tritium ($^3H$), iodine-125 ($^{125}I$) or C-14 ($^{14}C$). For another example, deuterated drugs can be formed by substituted hydrogen with deuterium. The bond between deuterium and carbon is stronger than that of ordinary hydrogen and carbon. Compared with non-deuterated drugs, deuterated drugs have advantages, such as reducing toxic side effects, increasing drug stability, enhancing the efficacy, and extending the biological half-life of drugs. All changes in the isotopic composition of the compounds of the present invention, whether radioactive or not, are included in the scope of the present invention. "Optional" or "optionally" means that the event or condition described thereafter may but not necessarily occur, and the description includes the situation where the event or condition occurs and the situation where the event or condition does not occur.

For drugs or pharmacologically active agents, the term "effective amount" or "therapeutically effective amount" refers to a sufficient amount of a medicine or agent that is non-toxic but can achieve the desired effect. For the oral dosage form of the present invention, the "effective amount" of one active substance in the composition refers to the amount required to achieve the desired effect when combined with another active substance in the composition. The determination of the effective amount varies from person to person, depending on the age and general conditions of the recipient, and also on the specific active substance. The appropriate effective amount in a case can be determined by those skilled in the art according to routine experiments.

The terms "active ingredient", "therapeutic agent", "active substance" or "active agent" refer to a chemical entity that can effectively treat the target disorder, disease or condition.

The term "substituted" means that any one or more hydrogen atoms on a specific atom are replaced by substituents, and may include deuterium and hydrogen variants, as long as the valence of the specific atom is normal and the substituted compound is stable. When the substituent is oxygen (i.e. =O), it means that two hydrogen atoms are substituted. Oxygen substitution does not occur on aromatic groups. The term "optionally substituted" means that it can be substituted or unsubstituted. Unless otherwise specified, the type and number of substituents can be arbitrary on the basis that they can be chemically realized.

When any variable (such as R) occurs more than once in the composition or structure of a compound, its definition in each situation is independent. Thus, for example, if a group is substituted with 0-2 R, the group can optionally be substituted with up to two R, and R has independent options in each situation. In addition, combinations of substituents and/or variants thereof are permitted only when such combinations will result in stable compounds.

When the number of a linking group is 0, such as —(CRR)$_0$—, it indicates that the linking group is a single bond.

When one of the variables is selected from a single bond, it means that the two groups connected thereby are directly connected. For example, when L in A-L-Z represents a single bond, it means that the structure is actually A-Z.

When a substituent is vacant, it means that the substituent is absent. For example, when X in A-X is vacant, it means that the structure is actually A. When it is not indicated which atom the listed substituent is connected to the substituted group, such substituent can be bonded via any atom. For example, a pyridyl group as a substituent can be attached to the substituted group through any one of the carbon atoms on pyridine ring.

When the linking direction of the linking group listed is not indicated, the linking direction is arbitrary. For example, in

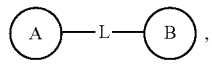

the linking group L is —MW—, and —MW— can connect ring A and ring B in the direction same to the reading order from left to right to form

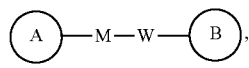

and also can connect ring A and ring B in the direction opposite to the reading order from left to right to form

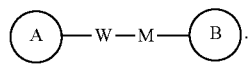

The combinations of the linking groups, substituents and/or its variants are permitted only when such combination will result in stable compounds.

Unless otherwise specified, the term "$C_{1-6}$ alkyl" is used to represent a linear or branched saturated hydrocarbon group containing 1 to 6 carbon atoms. $C_{1-6}$alkyl includes $C_{1-5}$, $C_{1-4}$, $C_{1-3}$, $C_{1-2}$, $C_{2-6}$, $C_{2-4}$, $C_6$ and $C_5$alkyl, and the like. It can be monovalent (such as methyl), divalent (such as methylene) or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "$C_{1-3}$ alkyl" is used to represent a linear or branched saturated hydrocarbon group containing 1 to 3 carbon atoms. $C_{1-3}$ alkyl includes $C_{1-2}$ and $C_{2-3}$ alkyl, and the like. It can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), and the like.

The term "leaving group" refers to a functional group or atom that can be substituted by another functional group or atom through a substitution reaction (for example, an nucleophilic substitution). For example, representative leaving groups include triflate; chlorine, bromine, iodine; sulfonate groups, such as mesylate, tosylate, p-bromobenzenesulfonate, p-tosylate, etc, acyloxy groups, such as acetoxy, trifluoroacetoxy and the like.

The term "protecting group" includes, but is not limited to, "amino protecting group", "hydroxy protecting group" or "sulfydryl protecting group". The term "amino protecting group" refers to a protecting group suitable for preventing side reactions at the nitrogen site of the amino. Representative amino protecting groups include but are not limited to: formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di (4'-methoxyphenyl)methyl; silyl, such as trimethylsilyl (TMS) and tert-butyldimethylsilyl (TBS) and so on. The term "hydroxy protecting group" refers to a protecting group suitable for preventing side reactions of the hydroxyl group. Representative hydroxy protecting groups include, but are not limited to: alkyl, such as methyl, ethyl, and tert-butyl; acyl, such as alkanoyl (such as acetyl); arylmethyl, such as benzyl (Bn), p-methyloxybenzyl (PMB), 9-fluorenylmethyl (Fm) and diphenylmethyl (diphenylmethyl, DPM); silyl such as trimethylsilyl (TMS) and tert-butyldimethylsilyl (TBS) and so on. The compounds of the present invention can be prepared by a variety of synthetic methods well known to those skilled in the art, including the specific embodiments listed below, the embodiments formed by their combination with other chemical synthesis methods, and equivalent alternatives well known to those skilled in the art. The preferred embodiments include but are not limited to the examples of the present invention.

The solvent used in the present invention is commercially available.

The present invention uses the following acronyms: CFU stands for the number of colonies; Boc stands for t-butoxycarbonyl; MIC stands for minimum inhibitory concentration.

DETAILED EMBODIMENTS

Figure 1:
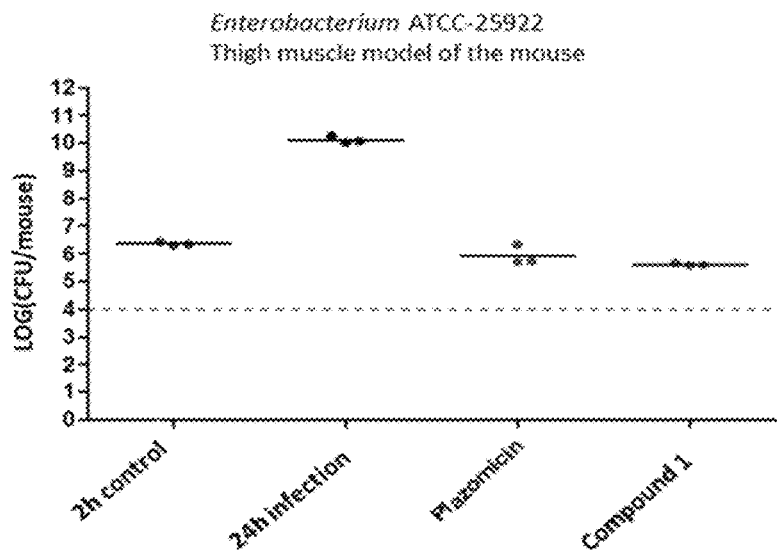
FIG. 1 shows the in vivo efficacy data of Compound 1 (at a dose of 30 mpk) and Plazomicin (at a dose of 30 mpk) in a mouse thigh muscle model (Enterobacteria ATCC-25922)

The present invention is described in detail through the following examples, which are not meant any adverse limitation to the present invention. While the present invention are described in detail herein with its specific embodiments being disclosed, various changes and improvements made thereto will be obvious for those skilled in the art without departing from the spirit and scope of the present invention.

Example 1: Compound 1

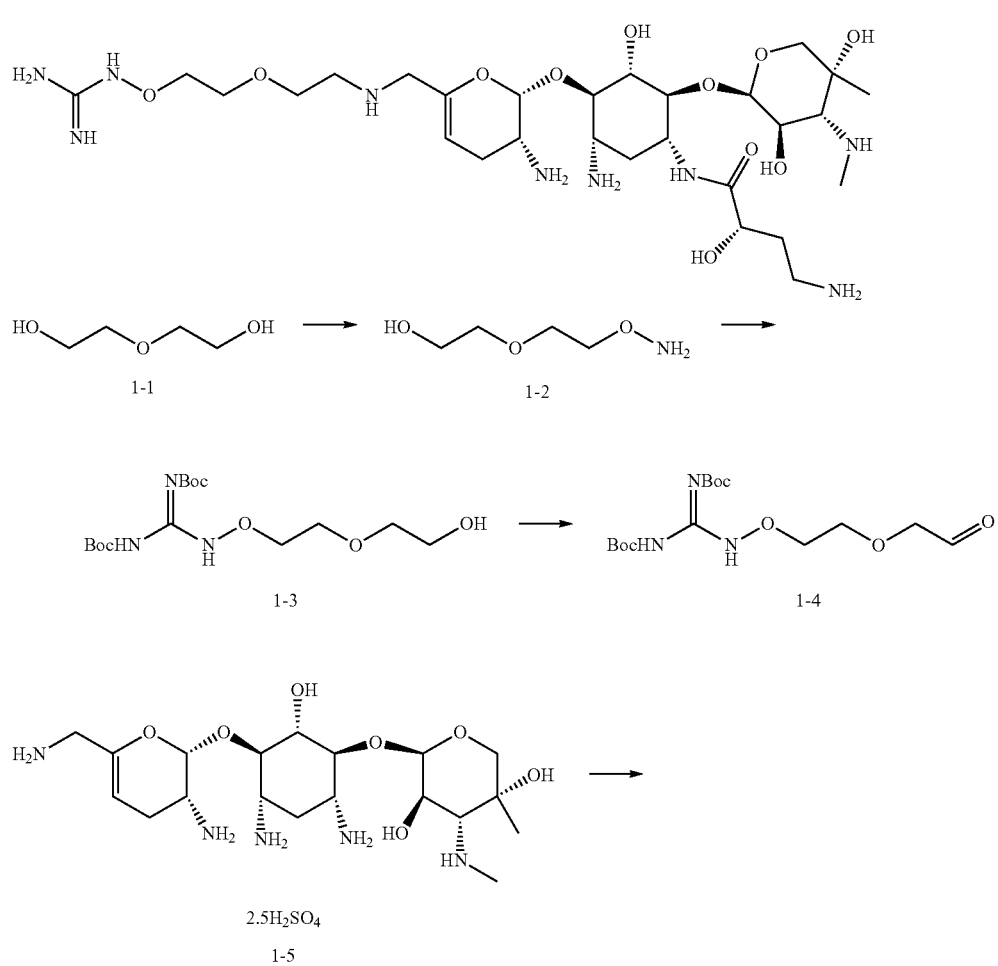

-continued
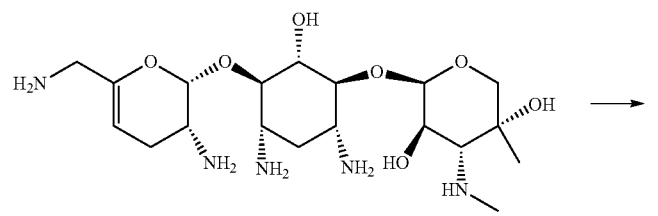
1-6
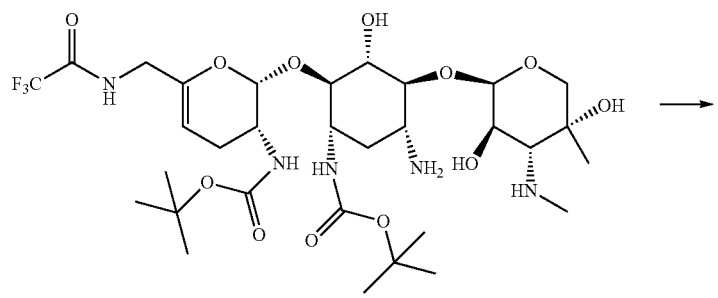
1-7
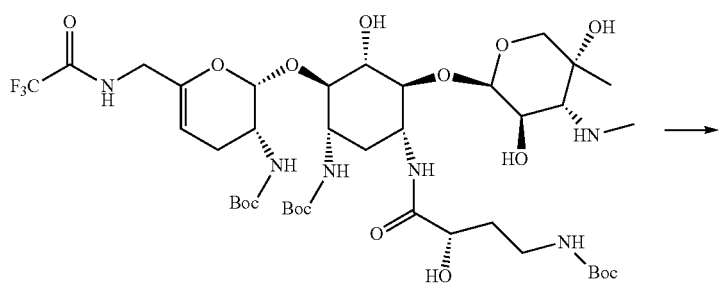
1-8
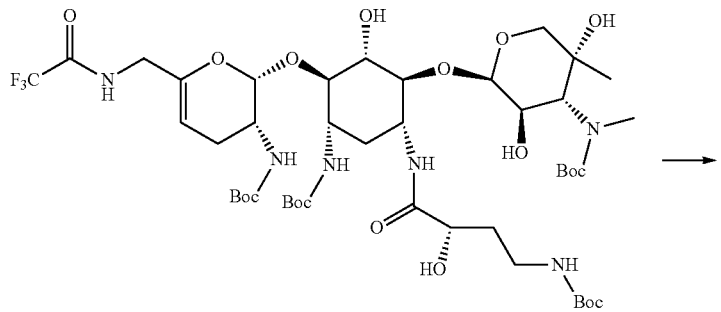
1-9
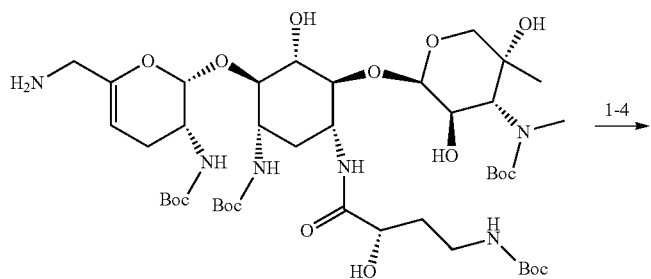
1-10

-continued

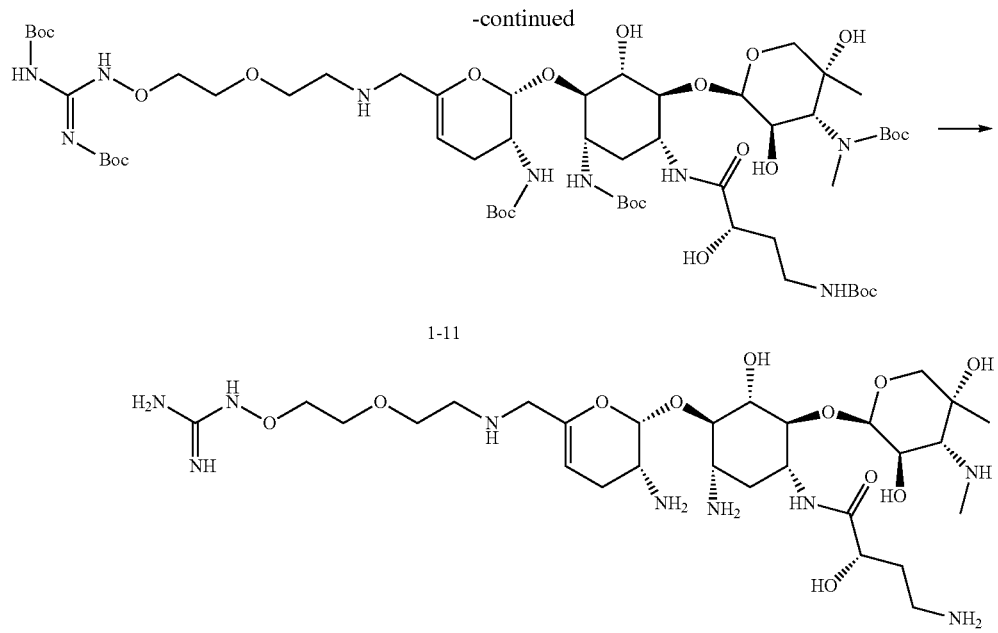

1-11

1

Diphenylphosphinyl hydroxylamine (10 g, 42.88 mmol, 1 eq), Compound 1-1 (13.65 g, 128.64 mmol, 12.19 mL, 3 eq) and sodium tert-butoxide (4.95 g, 51.46 mmol, 1.2 eq) were dissolved in tetrahydrofuran (100 mL), stirred and reacted at 5-15° C. for 16 hours. The reaction liquid was filtered, and the filtrate was concentrated to obtain Compound 1-2.

Step 2:

Compound 1-2 (5.19 g, 42.84 mmol, 1 eq) obtained in the previous step in tetrahydrofuran (100 mL) and N,N-di-BOC-1H-pyrazole-1-carboxamidine (13.30 g, 42.84 mmol, 1 eq) were stirred and reacted at 66° C. for 16 hours. The reaction liquid was cooled to room temperature, and extracted with ethyl acetate (100 mL×2) after water (300 mL) was added.

The organic phases were combined, dried over sodium sulfate and filtered. The filtrate was concentrated to obtain a crude product, and the Compound 1-3 was obtained through column chromatography (silica, petroleum ether/ethyl acetate=20/1, 1/1 (v/v)).

Step 3:

Compound 1-3 (1 g, 2.75 mmol, 1 eq) and 2-iodoxybenzoic acid (847.59 mg, 3.03 mmol, 1.1 eq) were dissolved in dimethyl sulfoxide (10 mL), and the reaction liquid was stirred at 40° C. for reaction 1 hour. The reaction liquid was filtered, and the filtrate was extracted with tert-butyl methyl ether (20 mL×2 times) after water (40 mL) was added. The organic phases were combined and washed with saturated sodium thiosulfate (10 mL). The organic phase was dried over anhydrous sodium sulfate, filtered and concentrated to obtain Compound 1-4.

Step 4:

Amberlite (ion exchange resin) IRA-402(OH) (500 g) was added to methanol (500 mL), and the solution was stirred at 20° C. for 1 hour. Then the mixture was filtered, the filter cake was added to methanol (500 mL), and then Compound 1-5 was added into this mixture. The mixture was stirred at 20° C. for 11 hours. During the reaction, Compound 1-5 dissolved. The reaction liquid was filtered, and the filtrate was concentrated to obtain Compound 1-6. LCMS (ESI) m/z: 448.4 (M+1).

Step 5:

Compound 1-6 (15 g, 33.52 mmol, 1 eq) was dissolved in methanol (150 mL), and then S-ethyl 2,2,2-trifluoroethyl thioester (4.24 g, 26.82 mmol, 0.8 eq) in methanol (150 mL) was added dropwise to the above methanol solution. The mixed solution was stirred at 20° C. for 16 hours. Then zinc acetate (14.72 g, 80.44 mmol, 2.4 eq) was added to the solution, and then (N-hydroxy-5-norbornene-2,3-dicarboxyl-imido)-tert-butyl ester (16.85 g, 60.33 mmol, 1.8 eq) and triethylamine (10.17 g, 100.55 mmol, 14.00 mL, 3 eq) in tetrahydrofuran (170 mL) were added dropwise to the mixed solution. The reaction liquid was stirred at 20° C. for 30 hours, then quenched with glycine (7 g), and then concentrated. The concentrated liquid was diluted with dichloromethane (1000 mL), and then washed twice with aqueous solution of (300 mL) (water:ammonia=7:3). The organic phase was concentrated. The crude product was purified by column chromatography (silica, dichloromethane/methanol=50/1-5/1 (v/v), containing a small amount of ammonia water) to obtain Compound 1-7. LCMS (ESI) m/z: 744.3 (M+1).

Step 6:

(2S)-4-(tert-butyloxycarbonylamino)-2-hydroxy-butyric acid (6.85 g, 31.26 mmol, 1.5 eq) was dissolved into N,N-dimethylformamide (150 mL) and N-hydroxy-5-norbornene-2,3-dicarboximide (5.60 g, 31.26 mmol, 1.5 eq) and 1-(3-dimethylaminopropyl)-3-ethylcarbodiimide (4.85 g, 31.26 mmol, 5.53 mL, 1.5 eq) were added to the solution. The reaction liquid was stirred at 20° C. for 2 hours, followed by adding Compound 1-7 (15.5 g, 20.84 mmol, 1 eq) therein. The reaction liquid was stirred at 20° C. for 16 hours, then diluted with water (200 mL), and extracted with ethyl acetate (50 mL×3). The combined organic phases were washed with saturated brine (100 mL), then dried over anhydrous sodium sulfate and filtered. The filtrate was concentrated to obtain a mixture. The mixture was purified by column chromatography (silica, dichloromethane/methanol=50/1-10/1 (v/v)) to obtain Compound 1-8. LCMS (ESI) m/z: 945.5 (M+1).

Step 7:

Compound 1-8 (16.40 g, 17.35 mmol, 1 eq), di-tert-butyl dicarbonate (4.55 g, 20.83 mmol, 4.78 mL, 1.2 eq), DIEA (2.69 g, 20.83 mmol, 3.6 mL, 1.2 eq) were dissolved in tetrahydrofuran (170 mL). Nitrogen replacement was performed for three times. The reaction liquid was stirred at 20° C. for 16 hours. The reaction liquid was diluted with water (200 mL), and then extracted with dichloromethane (100 mL×2). The combined organic phases were washed successively with 0.1M hydrochloric acid (20 mL) and saturated brine (60 mL), dried over anhydrous sodium sulfate, and filtered. The filtrate was concentrated to obtain a solid mixture. The mixture is purified by column chromatography (silica, petroleum ether/ethyl acetate=15/1-0/1 (v/v)) to obtain the target Compound 1-9. LCMS (ESI) m/z: 1045.3 (M+1).

Step 8:

Compound 1-9 (15.00 g, 14.35 mmol, 1 eq) and ammonia water (63.70 g, 1.82 mol, 70 mL, 126.62 eq) were dissolved in methanol (80 mL), and the mixture was stirred at 20° C. for 16 hours. The reaction liquid was concentrated to remove the solvent, diluted with water (100 mL), and extracted with dichloromethane (100 mL×3 times). The combined organic phases were washed with saturated brine (200 mL), dried over anhydrous sodium sulfate, and filtered. The filtrate was concentrated, and the concentrated mixture was purified by column chromatography (silica, first petroleum ether/ethyl acetate=10/1-0/1 (v/v), followed by dichloromethane/methanol=6/1 (v/v), the eluent contained a small amount of ammonia water) to obtain Compound 1-10. LCMS (ESI) m/z: 949.3 (M+1).

Step 9:

Compound 1-4 (50.63 mg, 0.15 mmol) and Compound 1-10 (145.00 mg, 0.15 mmol) were dissolved in methanol (5.00 mL), and then 4A molecular sieve (0.5 g) was added. The mixture was stirred for 0.5 hour at 18° C. under nitrogen atmosphere. Then sodium cyanoborohydride (19.20 mg, 0.30 mmol) was added and stirred for 1 hour. The completion of the reaction was detected by LCMS. The reaction liquid was filtered and concentrated, and separated by preparative-IPLC: Phenomenex Synergi C18 150×25 mm×10 μm; mobile phase: [water (0.225% formic acid)-acetonitrile]; acetonitrile %: 60%-90%, for 10 min to obtain Compound 1-11. LCMS (ESI) m/z: 1294.7 (M+1).

Step 10:

Compound 1-11 (91.00 mg, 71.97 mol) was dissolved in anhydrous dichloromethane (2.00 mL), cooled to 0° C. under nitrogen atmosphere. Trifluoroacetic acid (1.54 g, 13.51 mmol) was added and the reaction liquid was stirred at 0-19° C. for 9 hours, concentrated at room temperature, slurried with acetonitrile/methyl tert-butyl ether (4 mL, ⅓), filtered and concentrated to obtain Compound 1.

$^1$H NMR (400 MHz, D$_2$O) δ (ppm): 5.62 (s, 1H), 5.24 (s, 1H), 5.08 (s, 1H), 4.09-4.06 (m, 1H), 3.98-3.96 (m, 2H), 3.94-3.93 (m, 5H), 3.77-3.73 (m, 4H), 3.24 (s, 1H), 3.22-3.10 (m, 6H), 2.83 (s, 3H), 2.61-2.14 (m, 2H), 2.04-2.14 (m, 6H), 1.26 (s, 3H); LCMS (ESI) m/z: 664.5 (M+1).

Example 2: Compound 2

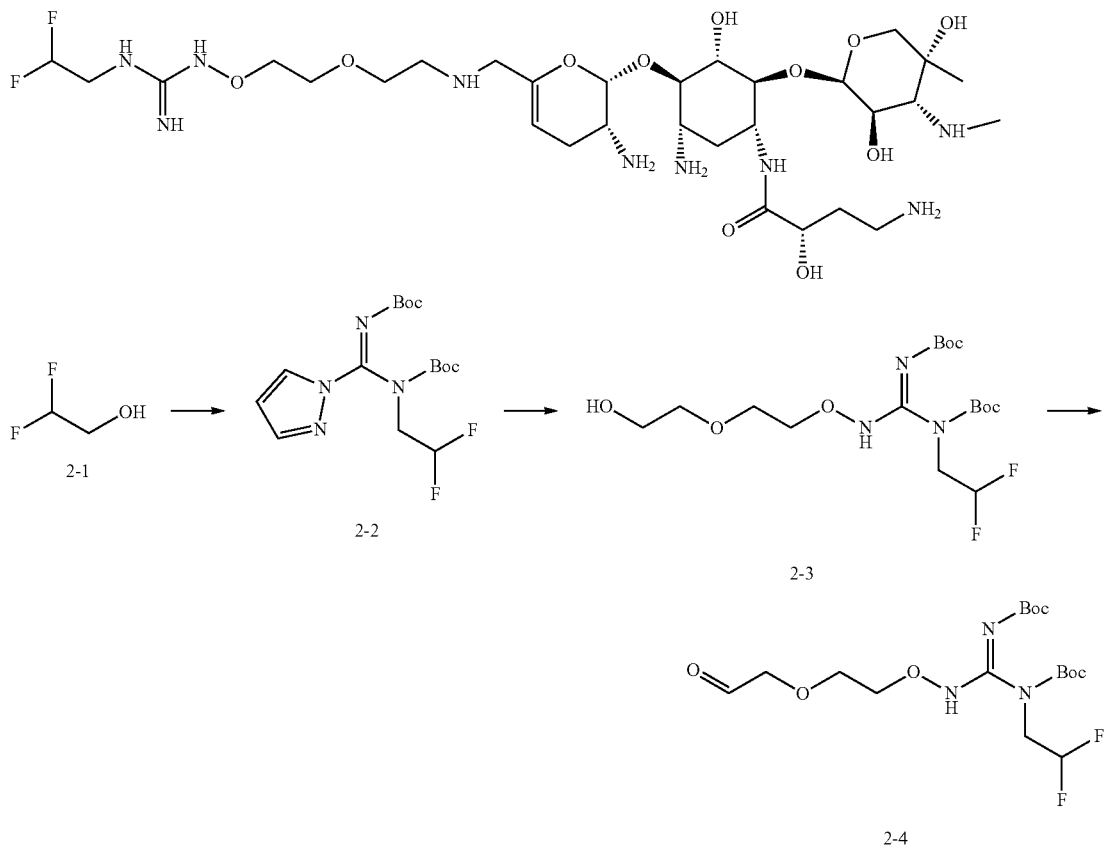

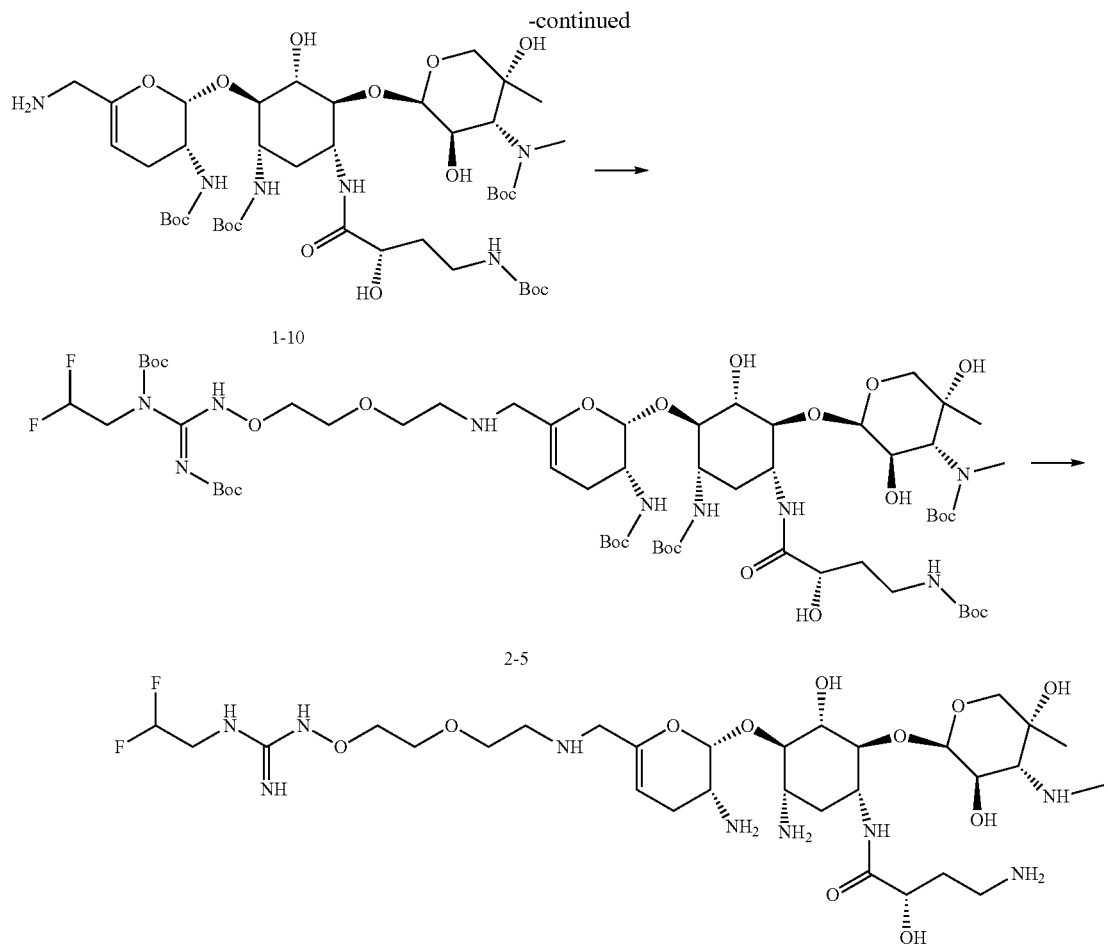

Step 1:

Compound 2-1 (1 g, 12.19 mmol, 71.94 µL, 1.2 eq), N,N-bis-BOC-1H-pyrazole-1-carboxamidine (3.15 g, 10.16 mmol, 1 eq) and triphenylphosphine (3.20 g, 12.19 mmol, 1.2 eq) were dissolved in tetrahydrofuran (40 mL), DIAD (2.46 g, 12.19 mmol, 2.37 mL, 1.2 eq) was added dropwise at 0° C. Then the mixture was heated to 20° C. and stirred for 12 hours. Water (100 mL) was added to the reaction solution, which was then extracted with ethyl acetate (50 mL, 3 times). The combined organic phases were washed with water (30 mL, 3 times), dried over anhydrous sodium sulfate, filtered and concentrated to obtain a crude product. The crude product was purified by chromatography column (silica, petroleum ether/ethyl acetate=50/1 to 20/1 (v/v)) to obtain Compound 2-2.

Step 2:

Compound 2-2 (3.25 g, 8.67 mmol, 0.5 eq) was added to Compound 1-2 (2.1 g, 17.34 mmol, 1 eq) in tetrahydrofuran (50 mL) at 20° C., and the reaction liquid was stirred at 67° C. for 12 hours. Water (100 mL) was added to the reaction liquid, which was then extracted with ethyl acetate (50 mL×3). The combined organic phases were washed with water (30 mL, 3 times), dried over anhydrous sodium sulfate, filtered and concentrated to obtain a crude product, which was purified by chromatography column (silica, petroleum ether/ethyl acetate=10/1 to 1/1 (v/v)) to obtain Compound 2-3.

Step 3:

2-Iodoxy benzoic acid (108.09 mg, 386.02 µmol, 1.1 eq) was added to Compound 2-3 (150 mg, 350.93 µmol, 1 eq) in dimethyl sulfoxide (3 mL) at 40° C. The reaction liquid was stirred at 40° C. for 2 hours. Saturated sodium bicarbonate/sodium thiosulfate (30 mL, (v/v)) was added to the reaction liquid, and the reaction liquid was extracted with ethyl acetate (20 mL×2). The combined organic phases were washed with saturated sodium bicarbonate/sodium thiosulfate (10 mL×3 times (1/1, v/v)), dried over anhydrous sodium sulfate, filtered and concentrated to obtain Compound 2-4.

Step 4:

Compound 2-5 (118 mg, 277.37 mol, 1.1 eq) and 4A molecular sieve (300 mg) were added to Compound 1-10 (239.32 mg, 252.16 mol, 1 eq) in 1,2-dichloroethane (2 mL) at 20° C. the mixture was stirred for 1 hour, and then sodium acetate borohydride (64.13 mg, 302.59 µmol, 1.2 eq) was added. The reaction liquid was stirred at 20° C. for 12 hours. with Water (20 mL) was added to the reaction liquid, which then was extracted with dichloromethane (20 mL×3). The combined organic phases were washed with water (10 mL×3), dried over anhydrous sodium sulfate, filtered and concentrated to obtain a crude product, which was then purified by preparative HPLC (column: Phenomenex Synergi C18 150×25 mm×10 µm; mobile phase: [water (0.225% formic acid)-acetonitrile]; acetonitrile %: 35%-56%, 7 min) to obtain Compound 2-6. LCMS (ESI) m/z: 1358.7 (M+1).

Step 5:

Compound 2-8 (40 mg, 29.44 μmol, 1 eq) was dissolved in dichloromethane (1 mL), and trifluoroacetic acid (1.54 g, 13.51 mmol, 1 mL, 458.70 eq) was added at 0° C. The reaction liquid was heated to 20° C. and stirred for 2 hours, and then cooled to 0° C. Methyl tert-butyl ether (15 mL) was added and the mixture was filtered, washed with methyl tert-butyl ether (2 mL×3), and dried with an oil pump at 40° C. to obtain Compound 2.

$^1$H NMR (400 MHz, D$_2$O) δ=6.18-5.87 (m, 1H), 5.63 (s, 1H), 5.28-5.22 (m, 1H), 5.08 (d, J=3.8 Hz, 1H), 4.23-4.16 (m, 1H), 4.09-4.03 (m, 3H), 3.98-3.89 (m, 2H), 3.83 (br t, J=5.2 Hz, 1H), 3.79-3.68 (m, 8H), 3.46-3.38 (m, 1H), 3.33 (br d, J=13.0 Hz, 1H), 3.26-3.22 (m, 2H), 3.16-3.07 (m, 2H), 2.83 (s, 3H), 2.69-2.55 (m, 1H), 2.42-2.29 (m, 1H), 2.19-2.06 (m, 2H), 1.95-1.85 (m, 1H), 1.83-1.71 (m, 1H), 1.29-1.23 (m, 3H).

LCMS (ESI) m/z: 758.3 (M+1).

Example 3: Compound 3

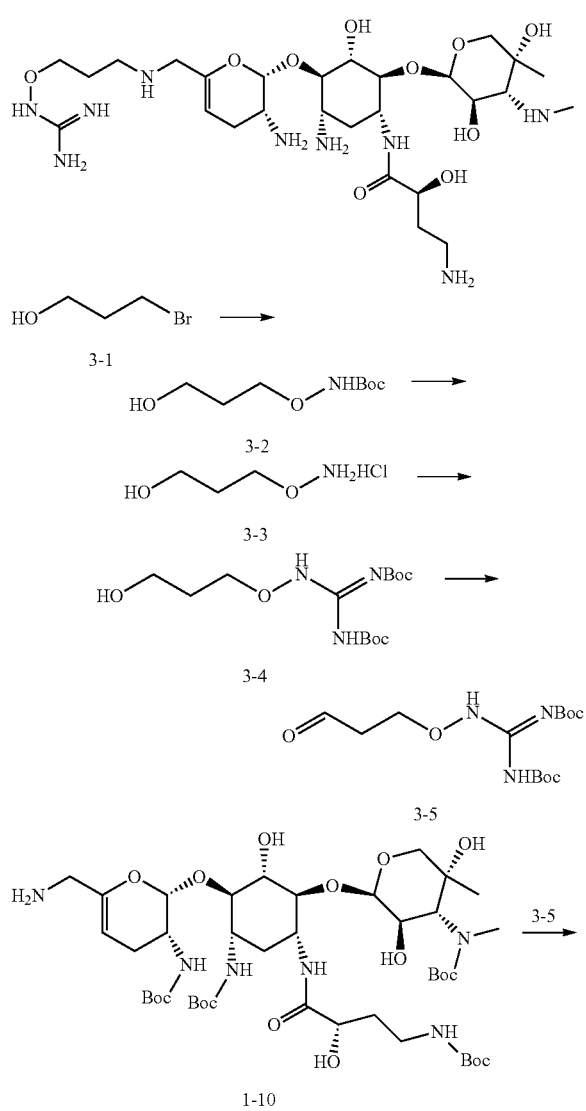

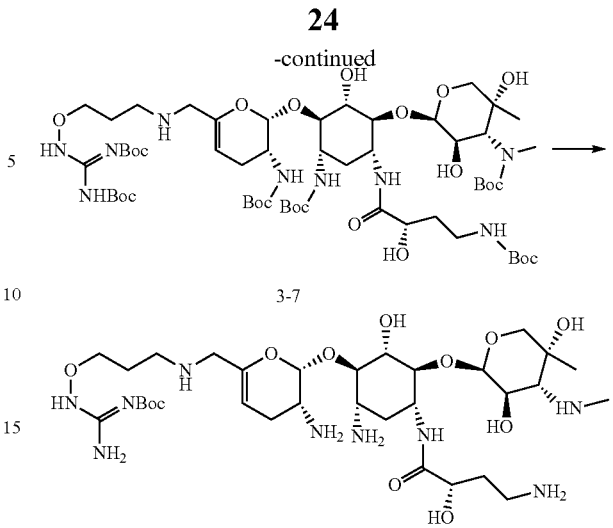

Step 1:

Compound 3-1 (16.00 g, 115.12 mmol) was dissolved in acetonitrile (200.00 mL), and N—BOC-hydroxylamine (15.33 g, 115.12 mmol) and DBU (19.28 g, 126.63 mmol) were added successively. The mixture was reacted at 11° C.-25° C. for 16 hours, and then concentrated. The residue was diluted with ethyl acetate (350 mL), washed with water (100 mL×3), washed with saturated brine (100 mL) once, dried over anhydrous sodium sulfate and concentrated. The residue was separated by column chromatography (filler: silica gel powder, eluent: ethyl acetate/petroleum ether=0-1/1 (v/v)) to obtain Compound 3-2.

Step 2:

Compound 3-2 (1.00 g, 5.23 mmol) and a solution of hydrogen chloride in dioxane (10 mL, 4 mmol) were mixed together and stirred at 20° C. for 16 hours, and then concentrated under reduced pressure to obtain Compound 3-3.

Step 3:

Compound 3-3 (581.27 mg, 6.38 mmol) and N,N-bis-Boc-1-guanylpyrazole (1.80 g, 5.8 mmol) were dissolved in tetrahydrofuran (20 mL) and triethylamine (1 mL) was added. The solution was stirred at 80° C. for 16 hours, and the completion of the reaction was detected by LCMS. The mixture was poured into water (100 mL), extracted with ethyl acetate (100 mL×3). The combined organic phases were washed with saturated brine (30 mL), dried over anhydrous sodium sulfate and concentrated. The residue was separated by column chromatography (filler: silica gel powder, eluent: ethyl acetate/petroleum ether=50/1-20/1 (v/v)) to obtain Compound 3-4.

Step 4:

2-Iodoxy benzoic acid (0.34 g, 1.2 mmol) was added to Compound 3-4 (0.40 g, 1.50 mmol) in dimethyl sulfoxide (5.00 mL), and the mixture was stirred at 40° C. for 3 hours under nitrogen atmosphere. The reaction liquid was diluted with ethyl acetate (100 mL), washed with water (50 mL×2) and saturated brine (50 mL) and concentrated. The residue was separated by column chromatography (filler: silica gel powder, eluent: ethyl acetate/petroleum ether=0-1/1) to obtain Compound 3-5.

Step 5:

4A molecular sieve (0.5 g) was added to Compound 3-5 (50.63 mg, 0.15 mmol) and Compound 1-10 (145.00 mg, 0.15 mmol) in methanol (5.00 mL). The mixture was stirred for 0.5 hour at 18° C. under nitrogen atmosphere, and then stirred for another 1 hour after sodium cyanoborohydride (19.20 mg, 0.30 mmol) was added. The completion of reaction was detected by LCMS. The reaction liquid was filtered and concentrated, and separated by preparative-HPLC: Phenomenex Synergi C18 150×25×10 μm; mobile phase: [water (0.225% formic acid))-acetonitrile]; acetonitrile %: 60%-90%, for 10 minutes to obtain Compound 3-7.

Step 6:

Compound 3-7 (91.00 mg, 71.97 mol) was dissolved in anhydrous dichloromethane (2.00 mL), cooled to 0° C. under nitrogen atmosphere. Trifluoroacetic acid (1.54 g, 13.51 mmol) was added, and the reaction liquid was stirred at 0-19° C. for 9 hours, concentrated at room temperature, and the residue was washed with acetonitrile/methyl tert-butyl ether (4 mL, ⅓) to obtain Compound 3.

$^1$H NMR (400 MHz, D$_2$O) δ (ppm): 5.62 (s, 1H), 5.24 (s, 1H), 5.08 (s, 1H), 4.09-4.06 (m, 1H), 3.98-3.96 (m, 2H), 3.94-3.93 (m, 5H), 3.77-3.73 (m, 4H), 3.24 (s, 1H), 3.22-3.10 (m, 6H), 2.83 (s, 3H), 2.61-2.14 (m, 2H), 2.04-2.14 (m, 6H), 1.26 (s, 3H): LCMS (ESI) m/z: 664.5 (M+1).

Biological Activity Assay

Experimental Example 1: Detection of Antibacterial Effect of Compound (MIC)

Three strains Enterobacteriaceae *E. coli* ATCC 25922, *E. coli* ATCC BAA-2523, *K. pneumonia* ATCC BAA-1705 were used to determine the Minimum Inhibitory Concentration (MIC) of each compound by the micro-liquid dilution method according to the requirements of the Institute of Clinical and Laboratory Standard (CLSI). 2-fold series diluted compounds (with a final concentration range 0.125 g/mL-128 g/mL) were added to a round bottom 96-well plate (Catalog #3788, Corning). A single clone of fresh bacteria on the plate of Mueller Hinton II Agar (MHA, Cat. No. 211438, BD BBL™) after overnight culture was picked and suspended in sterile saline to adjust the concentration to 1×10$^8$ CFU/mL, and then diluted to 5×10$^5$ CFU/mL by Cation-Adjusted Mueller Hinton II Broth (MHB, Catalog #212332, BD BBL™), 100 μL of which was added to the round bottom 96-well plate containing the drug. The plate was inverted and incubated at 37° C. for 20-24 hours, and the MIC value was read. The lowest drug concentration that inhibits bacterial growth was defined as MIC. The results are shown in Table 1.

TABLE 1

Antibacterial effect detection data (MIC) of the compounds of the present invention

| Strains | MIC (μM) | | |
|---|---|---|---|
| | *K. pneumoniae* ATCC BAA-1705 | *E. coli* ATCC BAA-2523 | *E. coli* ATCC 25922 |
| Compound 1 | 4 | 2 | 2 |
| Compound 2 | 4 | 4 | 2 |
| Compound 3 | 0.25 | 1 | 0.5 |

Conclusion: The compounds of the present invention have good in vitro antibacterial activity.

Experimental Example 2: Evaluation of Pharmacokinetics in Rats

Purpose of the Experiment:

To test the pharmacokinetic parameters of the compound of the present invention in rats Experimental Protocol:
1) Experimental drug: Compound 1;
2) Experimental animals: 3 male SD rats aged 7-9 weeks;
3) Drug preparation: An appropriate amount of the drug was weighed and dissolved in saline to forma 60 mg/mL solution.

Experimental Operation:

Animals were administered the drug at a dose of 150 mg/kg and a concentration of 60 mg/mL by a single intravenous drop infusion via the tail vein for 30 minutes. Plasma samples were collected from the animals at 0, 0.0333, 0.0833, 0.25, 0.5, 1, 2, 4, 6, 8 and 24 hours after administration. The LC-MS/MS method was used to determine the drug concentration in the plasma sample, and the kinetic parameters of the tested drug are shown in Table 2:

TABLE 2

Pharmacokinetic evaluation results of the compound of the present invention in rats

| Compound | Clearance Rate Cl (mL/Kg/min) | Maximum Concentration $C_{max}$ (nM) | Volume of Distribution Vd (L/Kg) | Half-Life $T_{1/2}$ (h) | Area Under the Curve AUC (nM · h) |
|---|---|---|---|---|---|
| Compound 1 | 9.48 | 315667 | 1.50 | 3.62 | 440373 |

Conclusion: The compound of the present invention has good pharmacokinetic properties in rats.

Experimental Example 3: Study on Pharmacokinetics in Mice

Purpose of the Experiment:

The purpose of this experiment is to evaluate the pharmacokinetic behavior of the compound after a single intravenous injection and intragastric administration, and to investigate the bioavailability after intragastric administration.

Experimental Operation:

CD-1 male mice aged 7 to 10 weeks were selected and treated by intravenous administration at the dose of 1 mg/kg. The mice were fasted for at least 12 hours before the administration, and resumed feeding 4 hours after the administration. The mice were free to drink during the entire experiment.

On the day of the experiment, the animals in the intravenous group were administered with corresponding compound by a single injection via tail vein with an administration volume of 5 mL/kg. The animals were weighed before the administration, and the administration volume was calculated based on the body weight. The sample collection time was: 0.083, 0.25, 0.5, 1, 2, 4, 8, and 24 h. Approximately 30 μL whole blood was collected through the saphenous vein at each time point to prepare plasma for high performance liquid chromatography-tandem mass spectrometry (LC-MS/MS) to determine the concentration.

All animals were subjected to euthanasia under $CO_2$ anesthesia after the PK samples at the last time point were collected. The non-compartmental model of the pharmacokinetic software WinNonlin™ Version 6.3 (Pharsight, Mountain View, CA) was used to process the data of plasma concentration, and the linear log-trapezoidal method was used to calculate the pharmacokinetic parameters.

Experimental results: The evaluation results of PK properties in mice are shown in Table 3.

TABLE 3

Evaluation of the pharmacokinetic properties of the compound of the present invention in mice

| Compound | Clearance Rate Cl (mL/Kg/min) | Maximum Concentration $C_{max}$ (nM) | Volume of Distribution Vd (L/Kg) | Half-Life $T_{1/2}$ (h) | Area Under the Curve AUC (nM · h) |
|---|---|---|---|---|---|
| Compound 1 | 15.1 | 7088 | 0.369 | 0.396 | 1924 |

Conclusion: The compound of the present invention has good pharmacokinetic properties in mice.

Experimental Example 4: Experimental Evaluation of Drug Efficacy in Mice (Mouse Thigh Muscle Model)

12 female CD-1 mice were divided into 4 cages, 3 mice per cage, and were injected intraperitoneally with the immunosuppressant cyclophosphamide (150 mpk).

24 hours later, 4 cages of mice were injected intraperitoneally again with the immunosuppressant cyclophosphamide (100 mpk). The strain E. coli ATCC-25922 (Enterobacteria ATCC-25922) was recovered on a MHA plate. The recovered colonies were picked and dissolved in saline to prepare E. coli ATCC-25922 bacterial solution with a concentration of 1.00E+07 CFU/mL for later use in mouse thigh muscle infection. The amount of bacterial solution injected into the thigh muscle of experimental mice was 100 L/mouse, that is, the inoculation amount was 1.00E+06 CFU/mouse. 2 h after infection, the thigh muscle tissue of the mice in control group was taken and placed in 10 mL saline, homogenized, and dotted on a plate with gradient dilution.

The specific administration of mice was as follows:
(1) 2 h after infection: At the end of 2 h infection, the thigh muscle tissue of the mice in the first cage was taken and placed in 10 mL saline, homogenized, and dotted on a plate with gradient dilution, two duplications for each mouse. The amount of bacteria loaded in the thigh muscle tissue of the mouse was counted. Mice in the third and fourth cages were injected respectively with 30 mpk Plazomicin and Compound 1 subcutaneously.
(2) 10 h after infection: Mice in the third and fourth cages were injected respectively with 30 mpk Plazomicin and Compound 1 subcutaneously. At the end of 24 h infection, the thigh muscle tissue of the mice in the second to fourth cages was taken and placed in 10 mL saline, homogenized, and dotted on a plate with gradient dilution, two duplications for each mouse. The amount of bacteria loaded in the thigh muscle tissue of the mouse was counted, and the experimental results were summarized and shown in FIG. 1.

Conclusion: The results in FIG. 1 show that Compound 1 at 30 mpk has better in vivo efficacy than Plazomicin.

Experimental Example 5: Experimental Evaluation of Drug Efficacy in Mice (Mouse Pneumonia Model)

21 CD-1 mice were divided into 7 cages, 3 mice per cage, and were injected intraperitoneally with the immunosuppressant cyclophosphamide (150 mpk) on the 4th day.

On the first day, 7 cages of mice were injected intraperitoneally again with the immunosuppressant cyclophosphamide (100 mpk). The strain Kpn ATCC-BAA-1705 (Klebsiella pneumoniae ATCC-BAA-1705) was recovered on a MHA plate. The recovered colonies were picked and dissolved in saline to prepare Kpn ATCC-BAA-1705 bacterial solution with a concentration of 4.00E+08 CFU/mL for later use in mouse lung infection. The amount of bacterial solution infected in the lung of experimental mice was 50 μL/mouse, that is, the inoculation amount was 2.00E+07 CFU/mouse. At 2 h and 24 h infection, the lung tissue of the mice in control group was taken and placed in 5 mL saline, homogenized, and dotted on a plate with gradient dilution.

The specific administration of mice was as follows:
(1) 2 h after infection: At the end of 2 h after infection, the lung tissue of the mice in the first cage was taken and placed in 5 mL saline, homogenized, and dotted on a plate with gradient dilution, two duplications for each mouse. The amount of bacteria loaded in the lung tissue of the mouse was counted. Mice in the third and fourth cages were injected respectively with 30 mpk and 10 mpk compound Plazomicin subcutaneously, mice in the fifth and sixth cages were injected respectively with 30 mpk and 10 mpk compound subcutaneously, and mice in the seventh cage were injected with 100 mpk meropenem subcutaneously.
(2) 10 h after infection: Mice in the third and fourth cages were injected respectively with 30 mpk and 10 mpk plazomicin subcutaneously, mice in the fifth and sixth cages were injected respectively with 30 mpk and 10 mpk compound 1 subcutaneously, and mice in the seventh cage were injected with 100 mpk meropenem subcutaneously. At the end of 24 h infection, the lung tissue of the mice in the second to seventh cages was taken and placed in 5 mL saline, homogenized, and dotted on a plate with gradient dilution, two duplications for each mouse. The amount of bacteria carried in the lung tissue of the mouse was counted, and the experimental results were summarized and shown in FIG. 2.

Figure 2:
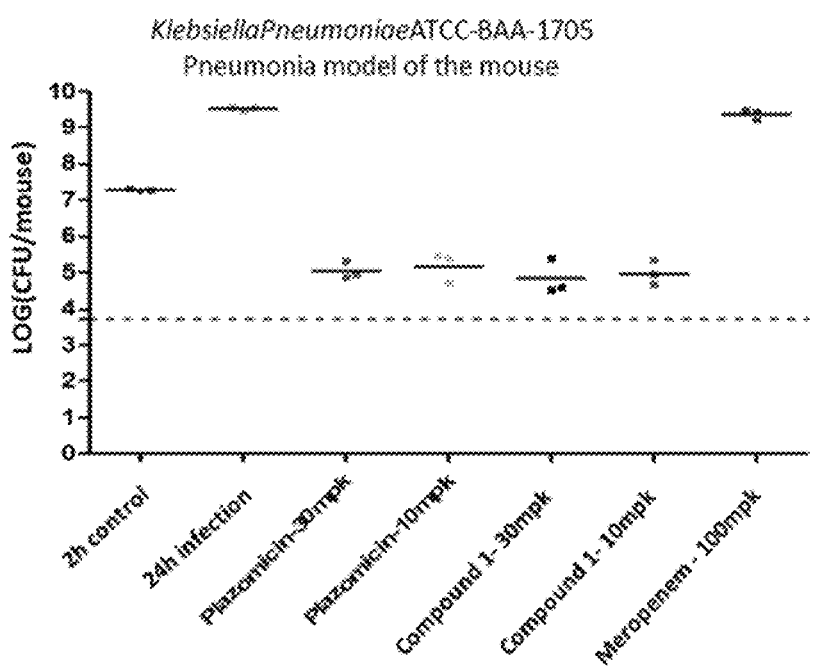
FIG. 2 shows the in vivo efficacy data of Compound 1 (at a dose of 10 mpk and 30 mpk), Plazomicin (at a dose of 10 mpk and 30 mpk), and Meropenem (at a dose of 100 mpk) in a mouse pneumonia model (*Klebsiella pneumoniae* ATCC-BAA-1705)

Conclusion: FIG. 2 shows that Plazomicin and Compound 1 has good in vivo activity in the Klebsiella pneumoniae strain 1705 lung infection model. At the same time, the efficacy of Compound 1 is better than that of Plazomicin, and the efficacy of Compound 1 at a dose of 10 mpk is equivalent to that of Plazomicin at a dose of 30 mpk.

Experimental Example 6: Research Report for Auditory Safety of the New Aminoglycoside Antibiotic Drugs Research Purposes:
To evaluate the effects of Compound 1 and the existing antibiotic plazomicin on auditory function in guinea pigs, and to evaluate the auditory toxicity of Compound 1.
Research Method:
Healthy adult guinea pigs (150-250 g) were employed as the research objects, and were randomly divided into saline control group, gentamicin group, compound Plazomicin group and Compound 1 group, with 8 animals in each group.

Subcutaneous administration is used, and the following assays were carried out during and after the administration for 14 consecutive days:
1. To analyze the effects of different drugs on the auditory function of guinea pigs, the compound action potential (CAP) of animals was recorded on the 14th day (29th day, i.e., 4 weeks) after administration. The results obtained were analyzed and the changes of the threshold shift, amplitude, latency and other indicators among different treatment groups were compared.
2. After the different groups of animals were processed and the auditory function data thereof were collected, the cochlea of the animals was taken out for fixation and staining. Surface preparation of basilar membrane of the cochlea on one side was performed to count the loss of hair cells so as to make a cochlea map, and the cochlea on the other side was decalcified and frozen sectioned. The density of spiral ganglion neurons was counted and compared among groups.

Research Results:

1. Administration Method and Treatment

Gentamicin from Dalian Meilun Biotechnology Co., Ltd., and Plazomicin and Compound 1 from WuXi AppTec (Wu-Han) Co., Ltd. are used, the solution of which were prepared just before use each time by using saline for dissolution to the concentration of 50 mg/mL, and the injection dose was 100 mg/kg body weight. Method: subcutaneous injection, and confirmation of no liquid leakage after each injection.

2. Analysis of Compound Action Potential (CAP)

The compound action potential (CAP) was tested and recorded when clicks and different frequencies of pure tones (1 KHz-32 kHz) were applied to each group of animals, and variations in amplitude and latency were mainly compared when clicks and medium and high frequency pure tones (16, 32 kHz) were applied. The magnitude of amplitude reflects the responsiveness of hair cells and auditory nerves. The larger the amplitude and the greater the slope of the I/O curve were, the better the responsiveness and the better the function were. In addition, the cochlea from apical turn to basal turn was responsive to sounds from low-frequency to high-frequency respectively, which is the frequency correspondence of the cochlear basilar membrane. The functional changes to different frequencies correspond to the different structural and functional changes of the cochlea fromapical turn to basal turn. The length of latency was also related to the function of the hair cells and auditory nerve response. Generally speaking, increasing of the threshold value when the cochlea was injured would inevitably lead to the extension of latency. In addition, the extension of latency when the threshold value did not change significantly also reflected the decrease in synchronicity of the auditory nerve discharge. In other words, the extension of latency reflected the decrease of response function. The previous ototoxicity of aminoglycoside antibiotics was mainly concentrated in the high-frequency area. In this study, the gentamicin group was consistent with previous results, as summarized below.

Figure 3:
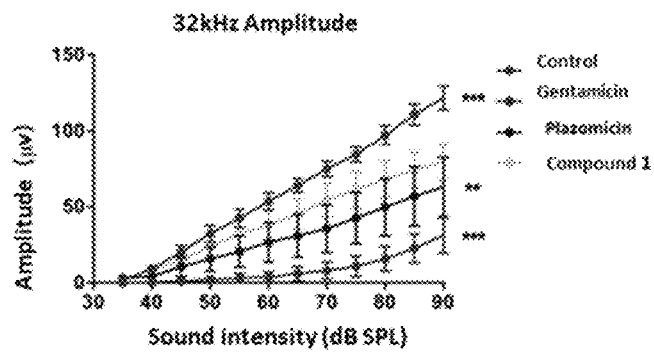
FIG. 3 shows the amplitude variations of the compound action potential: the variations of the CAP amplitude value of Compound 1, Gentamicin and Plazomicin at different intensities when the frequency was fixed at 32 kHz.
Figure 4:
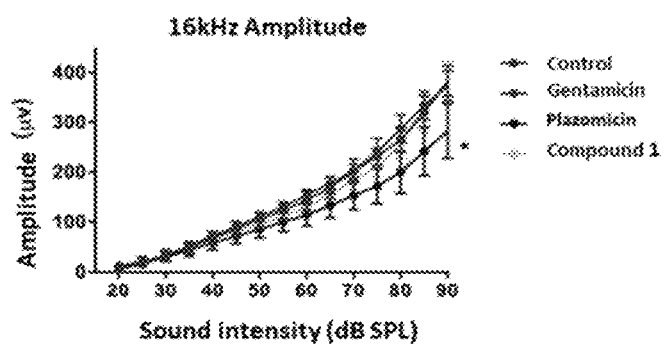
FIG. 4 shows the amplitude variations of the compound action potential: the variations of the CAP amplitude value of Compound 1, Gentamicin and Plazomicin at different intensities when the frequency was fixed at 16 kHz.
Figure 5:
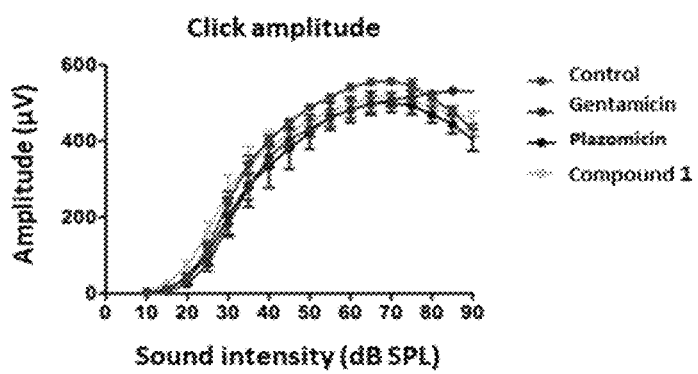
FIG. 5 shows the amplitude variations of the compound action potential: the variations of the CAP amplitude value of Compound 1, Gentamicin and Plazomicin at different intensities under a short sound (Click)

Compound 1 only caused a decrease of CAP amplitude of the experimental group in the high frequency (32 kHz), suggesting hearing damage in the high frequency area, but the amplitude was still higher than that of the Gentamicin and Plazomicin groups. The damage of Plazomicin group occurred in a wider range, damaged at both 16 kHz and 32 kHz, and the damage at 32 kHz greater than that of Compound 1, but significantly lower than that of the Gentamicin group. The damage of Gentamicin to the experimental group was concentrated in the high frequency (32 kHz) area, the threshold shift at 32 kHz was obvious, and the damage was more serious than the drugs of the other two groups (see FIGS. 3 to 5).

1) The amplitude results at 16 kHz showed that Compound 1 was no different from the Control group, while the Plazomicin group had 25.9% damage.
2) The CAP amplitude results at 32 kHz showed that Compound 1, Plazomicin and Gentamicin caused 34.7%, 48.2% and 74.3% hearing damage at 32 kHz, respectively, that is, Compound 1 still caused hearing damage at 32 kHz, which however was reduced by 13.5% and 39.6% respectively compared to Plazomicin and Gentamicin.
3) The CAP amplitude under click indicated that both Compound 1 and Gentamicin were consistent with the Control group, while Plazomicin caused hearing damage.

The specific values were as follows:
1) CAP amplitude at 16 kHz: Two-way ANOVA (Holm-Sidak method) showed that there were differences between the four groups of animals, F3, 570=7.858, p<0.001. Among them, there was no statistical difference in hearing between animals in the Compound 1 group, the Control group, and the Gentamicin group. The hearing of animals in the Plazomicin group was lower than that in the Control group (t=4.566, p<0.001), Gentamicin group (t=4.099, p<0.001) and Compound 1 group (t=2.799, p=0.021) respectively. *: p<0.05. The response of each group was maximum at 90 dB, at which the hearing of animals in Compound 1 group (381.646±20.895 uv) was significantly higher than that in the Plazomicin group (282.058±22.569 uv, t=2.799, p=0.021) and not significantly different from the Control group (383.130±19.545) and Gentamicin group (373.329±15.332 uv).
2) CAP amplitude at 32 kHz: Two-way ANOVA (Holm-Sidak method) showed that there are differences between the four groups of animals, F3, 570=100.611, p<0.001. The hearing of animals in the Compound 1 group was lower than that in the Control group (t=5.019, p<0.001), higher than the Plazomicin group (t=3.128, p=0.002) and Gentamicin group (t=10.484, p<0.001). The response of each group was maximum at 90 dB, at which, the hearing of the animals in the Compound 1 group (79.420±7.000 uv) was lower than that in the Control group (121.608±6.548 uv, t=4.401, p<0.001), higher than that in the Gentamicin group (31.272±5.137 uv, t=5.545, p<0.001) and Plazomicin group (62.982±7.561 uv, t=1.595, p=0.111).
3) CAP amplitude under click: Two-way ANOVA (Holm-Sidak method) showed differences among the four groups of animals, F3, 570=6.751, p<0.001. The hearing of animals in the Compound 1 group was significantly better than that in the Plazomicin group (t=3.493, p=0.003), and not significantly different between the Control group and the Gentamicin group.

In general, the results of CAP amplitude proved that the hearing damage of Compound 1 to experimental animals was significantly lower than that of Gentamicin and Plazomicin.

3. Variations in the Number of Hair Cells

Figure 6:
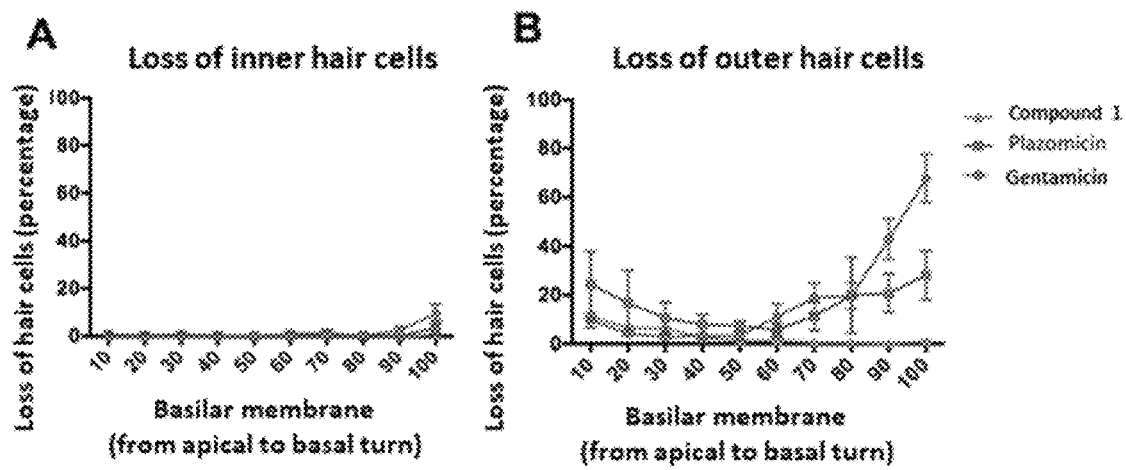
FIG. 6 shows the damage of cochlear hair cells: A shows the damage to inner hair cells of Compound 1, Gentamicin and Plazomicin; and B shows the damage to outer hair cells of Compound 1, Gentamicin and Plazomicin.

In order to compare the effects of different drugs on hair cells, hair cell staining and counting on the whole basilar membrane of the cochlea are performed. The results indicated that the Gentamicin group had 12-67.7% loss of outer hair cells in the medium and high frequency region (60-100% from the apical turn) and the loss was more obvious in the high frequency area. The Plazomicin group had 11.2-28.1% loss of outer hair cells in the high frequency (70-100% from the apical turn) and 16.7-24.2% loss of the outer hair cells at the beginning of the apical turn (10-20%). However, in the Compound 1 group, the loss of outer hair cells only occurred in the low-frequency region (from the top turn –40%), in which the loss rate of outer hair cells was about 2.5-11%, and the outer hair cells were relatively intact in the high frequency area (see FIG. 6 B). The specific values are shown in Table 4.

In the Compound 1 group, the inner hair cells were almost undamaged. Both the Plazomicin and Gentamicin groups had 3.5±3.0% and 9.3±4.1% loss of inner hair cells near the end of the basal turn (100% from the apical turn) respectively (see FIG. 6 A). The specific values are shown in Table 5.

In summary, the Compound group only had a slight loss of outer hair cells in the apical turn, and the rest part especially the basal turn and inner hair cells were preserved intact. The hair cell toxicity of Compound 1 was significantly lower than that of the Gentamicin and the Plazomicin.

4. Variations of Spiral Ganglion Neurons

Figure 7:
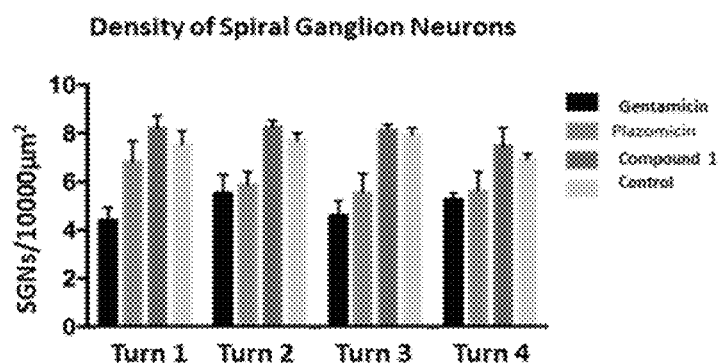
FIG. 7 shows the density variations of spiral ganglion neurons caused by Compound 1, Gentamicin and Plazomicin.
Figure 8:
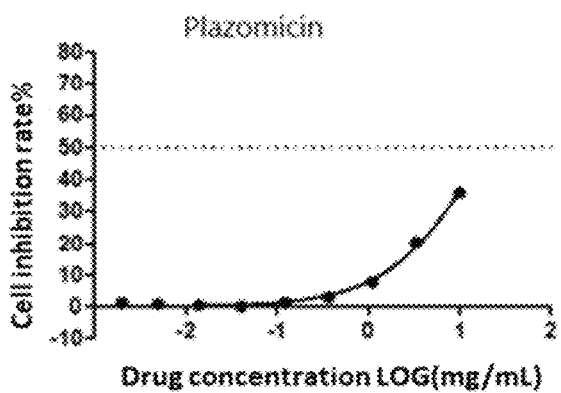
FIG. 8 shows the toxicity regression curve of Plazomicin on HK-2 cells.
Figure 9:
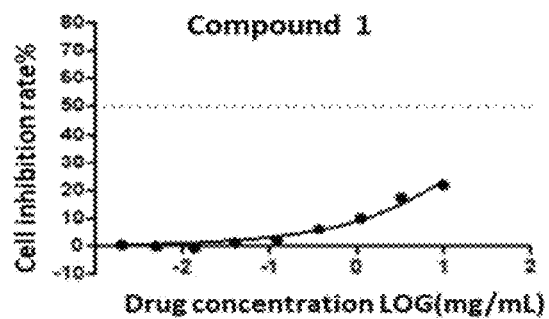
FIG. 9 shows the toxicity regression curve of Compound 1 on HK-2 cells.
Figure 10:
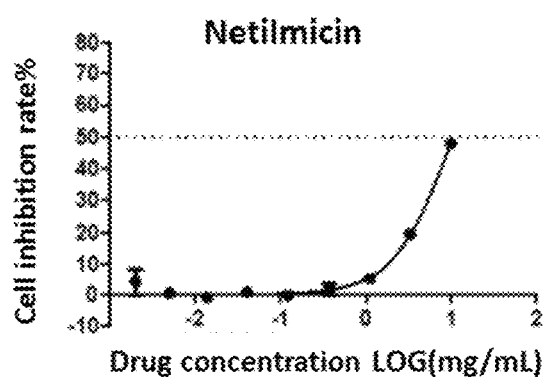
FIG. 10 shows the toxicity regression curve of Netilmicin on HK-2 cells.
Figure 11:
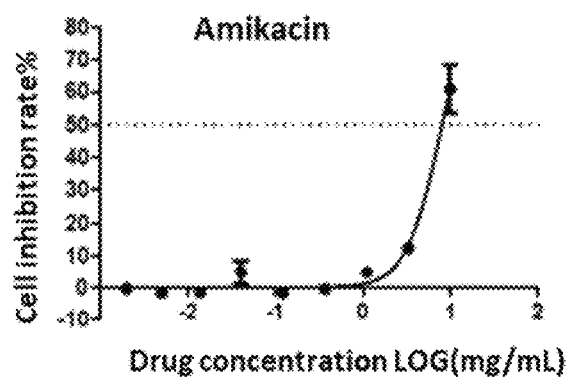
FIG. 11 shows the toxicity regression curve of Amikacin on HK-2 cells.

The cochlea of the guinea pig was defined as Turn 1, Turn 2, Turn 3, and Turn 4 from the basal to the apical turn. The spiral ganglion neurons (SGNs) were stained with TuJ on frozen sections, and the density thereof in a specific area were counted and compared between groups. There was no significant difference for the SGN density in each turn between the Compound 1 group and the Control group, that is, there was no damage to spiral ganglion neurons. The Gentamicin group had obvious damage in each turn. The Plazomicin group had a decrease in SGN density near the apical turn, but it was better than Gentamicin group. Through the two-way ANOVA, there was a significant difference between the groups, $F(3, 74)=35.43$, $p<0.0001$ (see FIG. 7). The specific values are shown in Table 6.

Conclusion: Based on the analysis of compound action potentials between different groups, it was confirmed that the Compound 1 group had hearing damage only at high frequency (32 kHz), which was better than the Plazomicin and Gentamicin groups. The observation of hair cells and spiral ganglion neurons confirmed that except for 2.5-11% loss of the outer hair cells near the apical turn, Compound 1 did not cause obvious damage to the outer hair cells in other areas, and the number of inner hair cells and the number of spiral ganglion neurons were not affected, which was significantly better than Gentamicin and Plazomicin groups. Therefore, Compound 1 was administered subcutaneously in animals (guinea pigs) for 14 consecutive days, and the ototoxicity thereof was less than that of the Plazomicin and Gentamicin after another 14 days. Based on the results of this study, it was confirmed that Compound 1 obtained by the present invention was better than Plazomicin and Gentamicin in terms of the auditory toxicity.

TABLE 4

Damage of outer ear hair cells on Day 29 (%, percentage)

| Damage percentage (%) | Compound 1 | Plazomicin | Gentamicin |
| --- | --- | --- | --- |
| 10 | 11.0 ± 1.3 | 24.4 ± 13.5 | 9.5 ± 2.9 |
| 20 | 6.3 ± 0.9 | 16.7 ± 13.4 | 4.1 ± 0.7 |
| 30 | 6.2 ± 1.1 | 10.5 ± 6.5 | 2.7 ± 0.7 |
| 40 | 2.5 ± 1.4 | 7.8 ± 4.0 | 3.2 ± 1.0 |
| 50 | 1.1 ± 0.8 | 7.2 ± 2.0 | 3.2 ± 1.5 |
| 60 | 1.4 ± 1.5 | 5.7 ± 5.1 | 12.6 ± 5.6 |

TABLE 4-continued

Damage of outer ear hair cells on Day 29 (%, percentage)

| Damage percentage (%) | Compound 1 | Plazomicin | Gentamicin |
| --- | --- | --- | --- |
| 70 | 0.7 ± 0.3 | 11.2 ± 11.8 | 13.6 ± 6.1 |
| 80 | 0.5 ± 0.3 | 19.9 ± 15.7 | 12.0 ± 5.4 |
| 90 | 0.2 ± 0.3 | 20.7 ± 7.9 | 42.8 ± 8.2 |
| 100 | 0.9 ± 0.7 | 28.1 ± 10.1 | 67.7 ± 9.8 |

TABLE 5

Damage of inner hair cells on Day 29 (%, percentage)

| Damage percentage (%) | Compound 1 | Plazomicin | Gentamicin |
| --- | --- | --- | --- |
| 10 | 0.3 ± 0.3 | 0.5 ± 0.4 | 0 |
| 20 | 0 | 0.3 ± 0.3 | 0 |
| 30 | 0 | 0.5 ± 0.5 | 0 |
| 40 | 0.1 ± 0.1 | 0.2 ± 0.2 | 0 |
| 50 | 0 | 0 | 0 |
| 60 | 0 | 0.8 ± 0.8 | 0.4 ± 0.4 |
| 70 | 0.3 ± 0.3 | 1.3 ± 1.3 | 0.6 ± 0.6 |
| 80 | 0 | 0 | 0.2 ± 0.2 |
| 90 | 0 | 0 | 2.5 ± 1.7 |
| 100 | 0.7 ± 0.5 | 3.5 ± 3.0 | 9.3 ± 4.1 |

TABLE 6

Density variation of spiral ganglion neurons on Day 29 (n/10000 μm$^2$)

| Turn | Gentamicin | Plazomicin | Compound 1 | Control |
| --- | --- | --- | --- | --- |
| Turn 1 | 4.407 ± 0.517 | 6.816 ± 0.852 | 8.230 ± 0.500 | 7.548 ± 0.534 |
| Turn 2 | 5.540 ± 0.757 | 5.876 ± 0.536 | 8.282 ± 0.254 | 7.695 ± 0.298 |
| Turn 3 | 4.604 ± 0.598 | 5.553 ± 0.793 | 8.136 ± 0.247 | 7.935 ± 0.292 |
| Turn 4 | 5.259 ± 0.280 | 5.641 ± 0.767 | 7.469 ± 0.772 | 6.936 ± 0.205 |

Experimental Example 7: Toxicity Test of the Compounds of the Present Invention on HK-2 Cells Cell Preparation:

On the day of the experiment, when the HK-2 cells in the culture flask reached 80%-90% confluent, the culture medium was discarded, the cells were washed twice with Dulbecco's phosphate buffered saline (DPBS) and digested for 1 to 2 minutes with 3 mL trypsin (T150 cell culture flask), and immediately 9 ml complete medium (RPMI1640+10% FBS) were added to terminate the digestion. After termination, single cells suspension were formed by pipetting gently, which were centrifuged at 1000 revolutions per second for 5 minutes. The supernatant was discarded, and fresh complete medium were added, and the cells were pipetted evenly. The actual cell density was measured according to the cell counter and the cell suspension was adjusted to $2.5 \times 10^5$ cells/mL. 80 μL of cell suspension was drawn by a row pipettor and added into a 96-well black bottom plate ($2 \times 10^4$ cell/well), and then incubated in a carbon dioxide incubator for 4.5 hours, which was defined as a cell plate.

Preparation of Compounds:

a. The compound mother liquor was prepared according to the following table, with complete medium as the solvent;

TABLE 7

Compound Information

| Compound | Mass (mg) | Purity (%) | Concentration (mg/mL) | Volume (μL) |
|---|---|---|---|---|
| Plazomicin | 5.88 | 99.65 | 50 | 117.19 |
| Compound 1 | 5.51 | 95 | 50 | 104.69 |
| Netilmicin | 5.00 | — | 50 | 100.00 |
| Amikacin | 5.74 | — | 50 | 114.80 | b. 50 microliters of complete medium was added into columns 3-11 in the 96-v well plate;

c. 75 microliters of test compound (50 mg/mL) and positive control were added to the second column of the 96-v well plate;

d. 25 microliters of compound was drawn from the second column and added into the third column, blown and sucked a few times by a row pipettor, then 25 microliters of liquid was drawn from the third column and added to the fourth column, and subsequently subjected to a 3-fold series dilution until the 10th column. From column 2 to column 11, the compound concentration was 50, 16.67, 5.56, 1.85, 0.62, 0.21, 0.07, 0.02, 0.008, 0 mg/mL;

e. 20 μL compound solutions of various concentrations prepared were transferred by a row pipettor to the corresponding wells of the cell plate, which was defined as a testing plate.

Culture of the Testing Plate:

All the plates were incubated in an incubator at 37° C., 5% $CO_2$ for 43 hours.

Reading:

After incubation, 10 microliters of Alma Blue was added to the testing plate. The testing plate was immediately incubated in an incubator at 37° C., 5% $CO_2$ for 3 hours. Then the fluorescence value of each well of the testing plate was read by a microplate reader (wavelength Ex 540 nm/Em 585 nm). Then prism software was used to simulate the curve to calculate $CC_{50}$ value.

Research Results:

TABLE 8

Experimental results and predicted $CC_{50}$

| Compound | $CC_{50}$ of HK-2 cell (mg/mL) | Maximum inhibition rate (%) | $CC_{50}$ of compound on cells predicted by software (Prism) (mg/mL) |
|---|---|---|---|
| Plazomicin | >10 | 35.98 | 19.53 |
| Compound 1 | >10 | 21.96 | 113.9 |
| Netilmicin | 10.64 | 48.73 | 10.64 |
| Amikacin | 8.157 | 68.40 | 8.156 |

Conclusion: The toxicity of compound 1 and Plazomicin to HK-2 cells was significantly lower than that of Netilmicin and Amikacin. In combination with the toxicity regression curve and software prediction (FIG. 8-11), the toxicity of Compound 1 to HK-2 cells was lower than Plazomicin.

What is claimed is:

1. A compound of the following formula, a pharmaceutically accentable salt thereof or a steroisomer thereof.

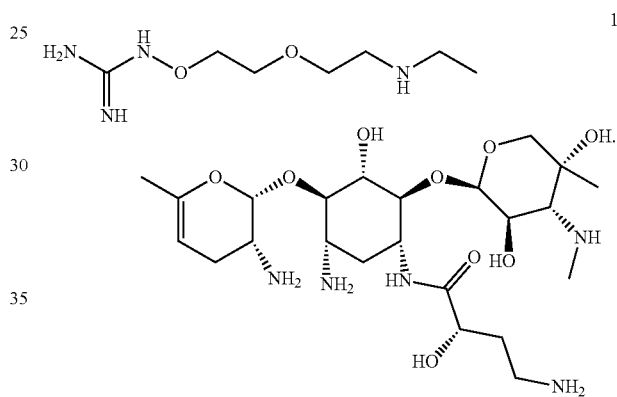

2. A pharmaceutical composition, comprising a therapeutically effective amount of the compound, the pharmaceutically acceptable salt thereof, or the steroisomer thereof according to claim 1 as an active ingredient, and a pharmaceutically acceptable carrier.

* * * * *